United States Patent
Patel et al.

(10) Patent No.: US 9,668,732 B2
(45) Date of Patent: Jun. 6, 2017

(54) SURGICAL STAPLER HANDLE ASSEMBLY HAVING ACTUATION MECHANISM WITH LONGITUDINALLY ROTATABLE SHAFT

(71) Applicant: Applied Medical Resources Corporation, Rancho Santa Margarita, CA (US)

(72) Inventors: Atal Patel, Rancho Santa Margarita, CA (US); Jonathan Covach, Mission Viejo, CA (US); Christina N. Reed, Rancho Santa Margarita, CA (US); Gary M. Johnson, Rancho Santa Margarita, CA (US); Matthew M. Becerra, Lake Forest, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 561 days.

(21) Appl. No.: 14/213,493

(22) Filed: Mar. 14, 2014

(65) Prior Publication Data

US 2014/0263562 A1    Sep. 18, 2014

Related U.S. Application Data

(60) Provisional application No. 61/794,700, filed on Mar. 15, 2013.

(51) Int. Cl.
*A61B 17/04* (2006.01)
*A61B 17/072* (2006.01)
(Continued)

(52) U.S. Cl.
CPC ...... *A61B 17/07207* (2013.01); *A61B 17/068* (2013.01); *A61B 2017/0046* (2013.01);
(Continued)

(58) Field of Classification Search
CPC ....... A61B 17/00; A61B 17/04; A61B 17/064; A61B 17/068; A61B 17/072; A61B 17/10;
(Continued)

(56) References Cited

U.S. PATENT DOCUMENTS

| 5,452,836 A | 9/1995 | Huitema et al. |
| 6,264,087 B1 | 7/2001 | Whitman |

(Continued)

OTHER PUBLICATIONS

The International Bureau of WIPO, International Preliminary Report on Patentability, dated Sep. 15, 2015, for International Application No. PCT/US2014/028811.

(Continued)

*Primary Examiner* — Gloria R Weeks
*Assistant Examiner* — William A Weller
(74) *Attorney, Agent, or Firm* — John F. Heal

(57) ABSTRACT

A handle assembly for a surgical stapler can comprise a rotatable actuation shaft. The actuation shaft can have a first rotational orientation in which it can actuate a jaw assembly in a repeatable open and close mode, a second rotational orientation in which it can actuate a jaw assembly in a staple firing mode, and a third rotational orientation in which it can actuate a jaw assembly in a reversing mode. The handle assembly can include a rotational mechanism arranged to discretely position the rotatable actuation shaft in one of the rotational orientations. The rotational mechanism can be arranged for single handed operation such as by including a slidable switch or selector to rotate the actuation shaft.

13 Claims, 18 Drawing Sheets

(51) Int. Cl.
*A61B 17/068* (2006.01)
*A61B 17/00* (2006.01)

(52) U.S. Cl.
CPC ............... *A61B 2017/00477* (2013.01); *A61B 2017/07257* (2013.01)

(58) Field of Classification Search
CPC ............ A61B 17/285; A61B 17/00367; A61B 17/00407; A61B 17/07207
USPC ..................................................... 227/178.1
See application file for complete search history.

(56) References Cited

U.S. PATENT DOCUMENTS

| | | | |
|---|---|---|---|
| 6,644,532 B2 | 11/2003 | Green et al. | |
| 6,821,282 B2 | 11/2004 | Perry et al. | |
| 6,905,057 B2* | 6/2005 | Swayze | A61B 17/07207 227/176.1 |
| 7,111,769 B2* | 9/2006 | Wales | A61B 17/07207 227/175.1 |
| 7,490,749 B2* | 2/2009 | Schall | A61B 17/07207 227/176.1 |
| 7,753,246 B2* | 7/2010 | Scirica | A61B 17/07207 227/175.1 |
| 7,810,690 B2* | 10/2010 | Bilotti | A61B 1/0014 227/175.1 |
| 7,963,431 B2* | 6/2011 | Scirica | A61B 17/07207 227/175.1 |
| 8,056,787 B2* | 11/2011 | Boudreaux | A61B 17/07207 227/175.1 |
| 8,061,576 B2* | 11/2011 | Cappola | A61B 17/072 227/175.1 |
| 8,100,309 B2 | 1/2012 | Marczyk | |
| 8,236,010 B2 | 8/2012 | Shelton et al. | |
| 8,281,972 B2 | 10/2012 | Wixey et al. | |
| 9,314,247 B2* | 4/2016 | Shelton, IV | A61B 17/00491 |
| 2005/0234478 A1 | 10/2005 | Wixey | |
| 2006/0097026 A1 | 5/2006 | Shelton, IV | |
| 2007/0068990 A1 | 3/2007 | Shelton, IV | |
| 2007/0295780 A1* | 12/2007 | Shelton | A61B 17/0682 227/176.1 |
| 2008/0255607 A1 | 10/2008 | Zemick | |
| 2012/0080482 A1 | 4/2012 | Schall et al. | |
| 2012/0239012 A1* | 9/2012 | Laurent | A61B 17/068 606/1 |
| 2013/0015230 A1 | 1/2013 | Wixey | |
| 2013/0098969 A1 | 4/2013 | Scirica et al. | |
| 2013/0105545 A1 | 5/2013 | Burbank | |
| 2014/0021239 A1 | 1/2014 | Kostrzewski | |

OTHER PUBLICATIONS

International Searching Authority/US, The International Search Report and the Written Opinion of the International Searching Authority for International Application No. PCT/US2014/028811, titled Surgical Stapler Having Actuation Mechanism with Rotatable Shaft, mailed Aug. 5, 2014.
Ethicon Endo Surgery, Inc., Contour Curved Cutter Stapler, 2014.
Justright Surgical, JustRight Surgery, Dec. 31, 2014.

* cited by examiner

SURGICAL STAPLER HANDLE ASSEMBLY HAVING ACTUATION MECHANISM WITH LONGITUDINALLY ROTATABLE SHAFT

CROSS REFERENCE TO RELATED APPLICATIONS

This application claims the benefit of U.S. Provisional Patent Application Ser. No. 61/794,700, entitled "SURGICAL STAPLER HAVING ACTUATION MECHANISM WITH ROTATABLE SHAFT," filed on Mar. 15, 2013. The entirety of this prior application is hereby incorporated herein by reference.

BACKGROUND OF THE INVENTION

Field of the Invention

The present application relates generally to surgical occlusion instruments and, more particularly, to surgical staplers.

Description of the Related Art

Surgical staplers are used to approximate or clamp tissue and to staple the clamped tissue together. As such, surgical staplers have mechanisms to ensure that tissue is properly positioned and captured and to drive staples through the tissue. As a result, this has produced, for example, multiple triggers and handles in conjunction with complex mechanisms to provide proper stapling of the clamped tissue. With these complex mechanisms, surgical staplers can have increased manufacturing burdens, as well as potential sources for device failure and confusion for the user. Thus, reliable stapling of clamped tissue without complex mechanisms is desired.

SUMMARY OF THE INVENTION

In certain embodiments, a surgical stapler is provided herein. The surgical stapler comprises an elongate shaft, a jaw assembly, and a handle assembly. The elongate shaft has a proximal end and a distal end. The elongate shaft defines a longitudinal axis between the proximal end and the distal end. The jaw assembly is positioned at the distal end of the elongate shaft. The jaw assembly comprises a first jaw, a second jaw, and a plurality of staples. The jaw assembly is selectively positionable in one of a closed configuration, an open configuration, and a firing configuration. The handle assembly is positioned at the proximal end of the elongate shaft. The handle assembly comprises a stationary handle, a movable trigger pivotably coupled to the stationary handle, and an actuation shaft. The actuation shaft is longitudinally slidable within the handle assembly with respect to the longitudinal axis of the actuation shaft and rotatable within the handle assembly with respect to the longitudinal axis. The actuation shaft is operably coupled to the jaw assembly and the actuation shaft is longitudinally slidable in a first direction from a first position corresponding to the open configuration of the jaw assembly to a second position corresponding to the closed configuration of the jaw assembly and from the second position to a third position corresponding to the firing configuration. The actuation shaft is operably coupled to the movable trigger. The actuation shaft is rotatable between a first orientation in which movement of the trigger moves the actuation shaft between the second position and the third position and a second orientation in which movement of the trigger moves the actuation shaft from the third position to the first position.

In certain embodiments, a handle assembly for a surgical stapler is provided. The surgical stapler comprises an elongate shaft having a proximal end and a distal end, the elongate shaft defining a longitudinal axis between the proximal end and the distal end, and a jaw assembly disposed at the distal end of the elongate shaft. The handle assembly comprises a housing, a stationary handle disposed on the housing, a movable handle, an actuation mechanism, and a coupler. The movable handle is pivotably coupled to the housing and pivotable between an open position spaced apart from the stationary handle and a closed position adjacent the stationary handle. The actuation mechanism comprises an advancing driver, a reversing driver, and an actuation shaft. The advancing driver is operably coupled to the movable handle and translatable distally with respect to the longitudinal axis responsive to movement of the movable handle from the open position to the closed position. The reversing driver is operably coupled to the movable handle and translatable proximally with respect to the longitudinal axis responsive to movement of the movable handle from the open position to the closed position. The actuation shaft extends along the longitudinal axis. The actuation shaft is rotatably coupled to the housing with respect to the longitudinal axis. The actuation shaft comprises an advancing surface and a reversing surface. The advancing surface extends longitudinally along the actuation shaft. The reversing surface extends longitudinally along the actuation shaft. The reversing surface is angularly offset from the advancing surface. The actuation shaft is rotatable between a first orientation in which the advancing driver engages the advancing surface and a second orientation in which the reversing driver engages the reversing surface. The coupler is adapted to engage the elongate shaft of the surgical stapler.

In certain embodiments, a handle assembly for a surgical stapler is provided. The handle assembly comprises a housing, a trigger pivotably coupled to the housing, and an actuation mechanism. The actuation mechanism comprises a forward driver, a reverse driver, an actuation shaft, and a selector. The forward driver is operably coupled to the trigger. The reverse driver is operably coupled to the trigger. The actuation shaft has a longitudinal axis. The actuation shaft is rotatably coupled to the housing relative to the longitudinal axis. The actuation shaft comprises a forward interface surface and a reverse interface surface angularly offset from the forward interface surface. The actuation shaft is rotatable between a first orientation in which the forward interface surface engages the forward driver to move the actuation shaft in a first direction responsive to pivotal movement of the trigger and a second orientation in which the reverse interface surface engages the reverse driver to move the actuation shaft in a second direction opposite the first direction responsive to pivotal movement of the trigger. The selector is operably coupled to the actuation shaft to selectively rotate the actuation shaft between the first orientation and the second orientation.

DETAILED DESCRIPTION OF THE INVENTION

Figure 1:
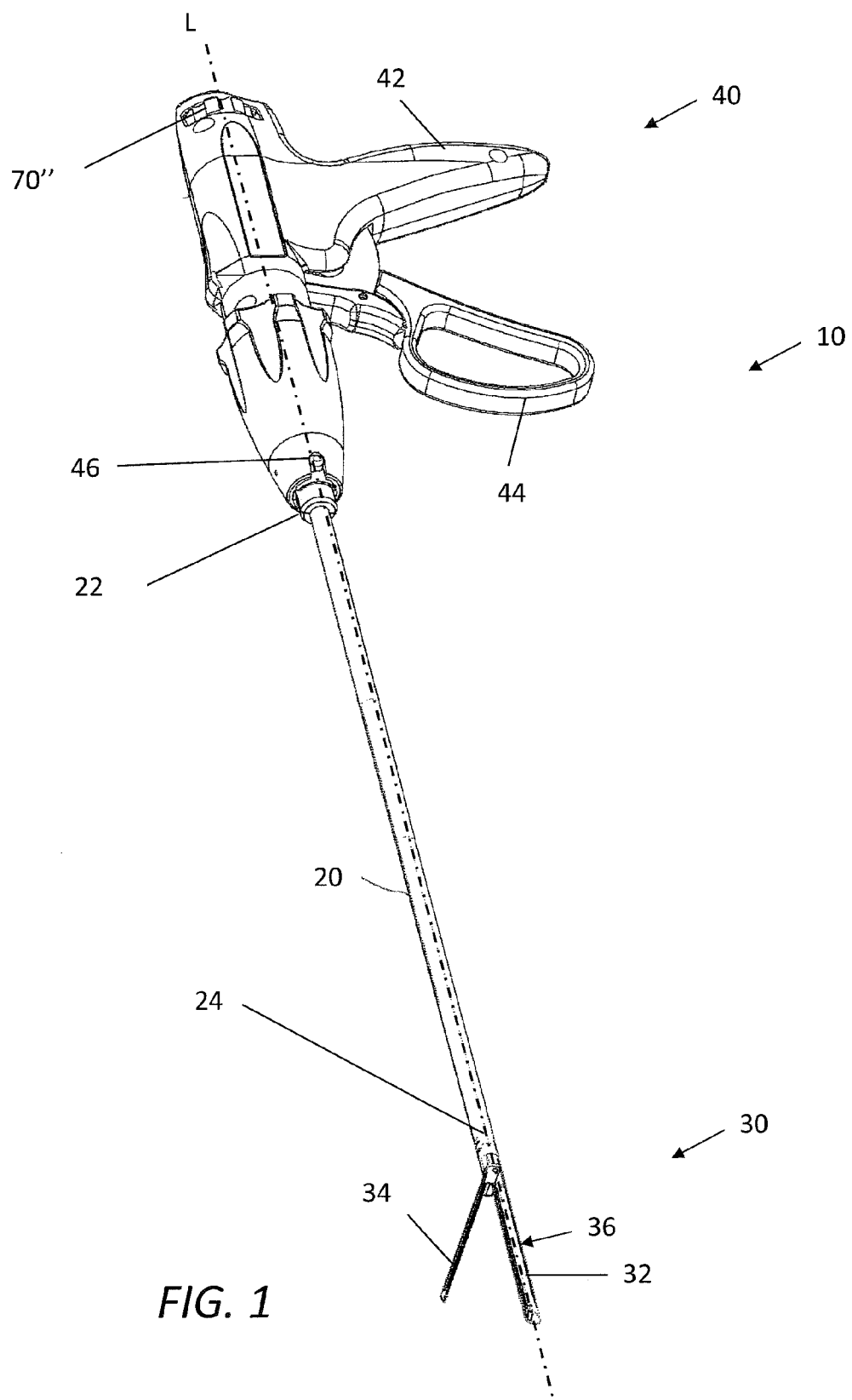
FIG. 1 is a perspective view of an embodiment of surgical stapling device with the jaws in an open configuration.
Figure 2:
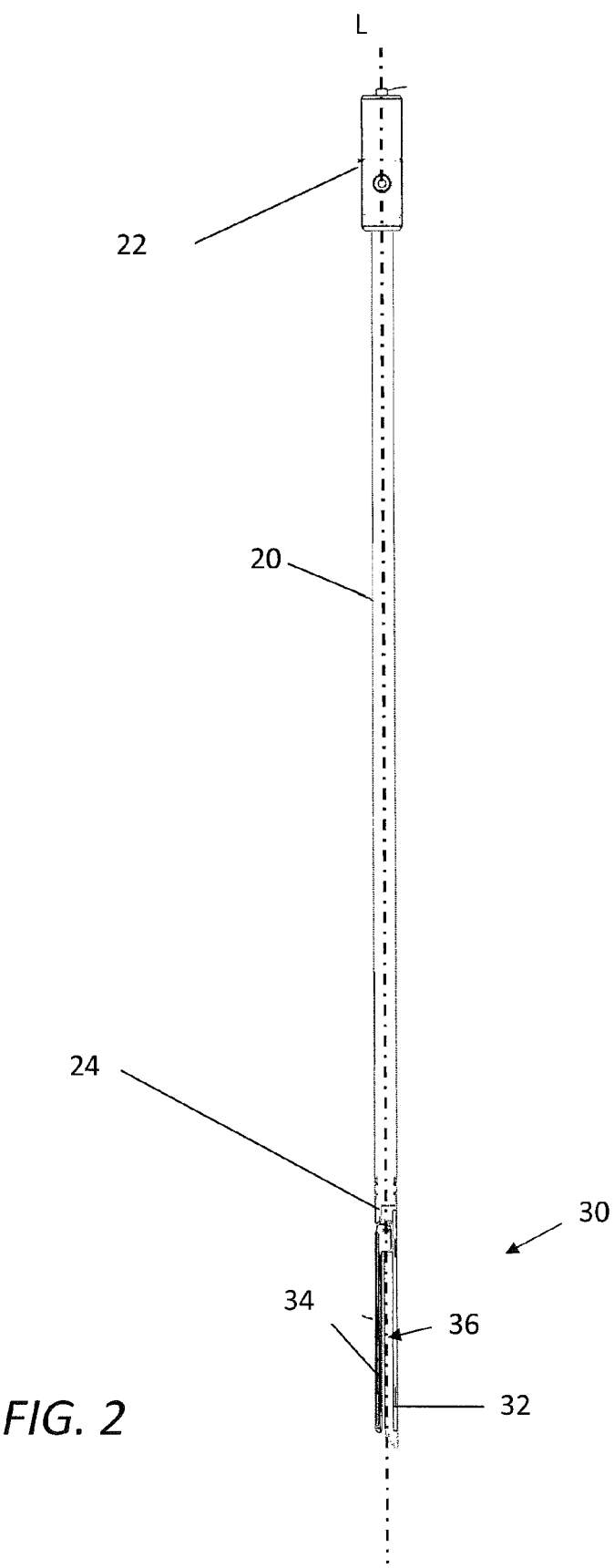
FIG. 2 is a perspective view of an embodiment of a cartridge for the surgical stapling device of FIG. 1 with the jaws in a closed configuration.

With reference to FIGS. 1-2, an embodiment of surgical stapling device is illustrated. The illustrated embodiment of surgical stapler 10 comprises an elongate shaft 20, a jaw assembly 30, and a handle assembly 40. FIG. 1 illustrates the surgical stapler 10 with the jaw assembly 30 in an open configuration. FIG. 2 illustrates a removable cartridge comprising the elongate shaft 20 and jaw assembly 30 of the surgical stapler 10 with the jaw assembly 30 in a closed configuration.

With continued reference to FIGS. 1 and 2, the illustrated embodiment of surgical stapler 10 can be sized and configured for use in laparoscopic surgical procedures. For example, the elongate shaft 20 and jaw assembly 30 can be sized and configured to be introduced into a surgical field through an access port or trocar cannula. In some embodiments, the elongate shaft 20 and jaw assembly 30 can be sized and configured to be inserted through a trocar cannula having a relatively small working channel diameter, such as, for example, less than 8 mm. In other embodiments, elongate shaft 20 and jaw assembly 30 can be sized and configured to be inserted through a trocar cannula having a larger working channel diameter, such as, for example, 10 mm, 11 mm, 12 mm, or 15 mm. In other embodiments, it is contemplated that certain aspects of the surgical staplers described herein can be incorporated into a surgical stapling device for use in open surgical procedures.

With continued reference to FIGS. 1 and 2, as illustrated, the elongate shaft 20 comprises a generally tubular member. The elongate shaft 20 extends from a proximal end 22 to a distal end 24. Elongate shaft 20 defines a central longitudinal axis, L. of the surgical stapler 10 extending between the proximal end 22 and the distal end 24.

With continued reference to FIGS. 1 and 2, in the illustrated embodiment, the jaw assembly 30 is coupled to the elongate shaft 20 at the distal end 24 of the elongate shaft 20. The jaw assembly 30 comprises a first jaw 32 and a second jaw 34 pivotally coupled to the first jaw 32. In the illustrated embodiment, the first jaw 32 is fixed to the distal end 24 of elongate shaft 20 such that it extends distally along the central longitudinal axis, L and remains stationary with respect to the elongate shaft 20. In other embodiments, it is contemplated that the jaw assembly 30 is articulable with respect to the elongate shaft 20. In an initial configuration, the first jaw 32 includes a plurality of staples 36 disposed therein.

With continued reference to FIGS. 1 and 2, in the illustrated embodiment, the jaw assembly 30 can be actuated from an open configuration (FIG. 1) to a closed configuration (FIG. 2) to a stapling configuration by an actuation member or beam that is longitudinally slidable within the elongate shaft. In an initial position, the beam can be positioned at the distal end 24 of the elongate shaft 20. With the beam in the initial position, the second jaw 34 is pivoted away from the first jaw 32 such that the jaw assembly 30 is in the open configuration. The actuation beam engages the second jaw 34 upon translation of the actuation member or beam distally along the longitudinal axis L. Translation of the actuation beam distally from the initial position a first distance can actuate the jaw assembly from the open configuration to the closed configuration. With the jaw assembly 30 in the closed configuration, the actuation beam can be returned proximally the first distance to return the jaw assembly 30 to the open configuration. A distal end of the actuation beam can advance a staple slider configured to deploy staples from the first jaw 32 such that further translation of the actuation beam distally past the first distance deploys the plurality of staples 36 from the first jaw 32.

With continued reference to FIGS. 1 and 2, in the illustrated embodiment, the handle assembly is coupled to the elongate shaft 20 at the proximal end 22 of the elongate shaft 20. As illustrated, the handle assembly 40 has a pistol grip configuration with a housing defining a stationary handle 42 and a movable handle 44 or trigger pivotably coupled to the stationary handle 42. It is contemplated that in other embodiments, surgical stapler devices including aspects described herein can have handle assemblies with other configuration such as, for example, scissors-grip configurations, or in-line configurations. As further described in greater detail below, the handle assembly 40 houses an actuation mechanism configured to selectively advance an actuation shaft responsive to movement of the movable handle 44.

In some embodiments, the surgical stapler 10 can include the plurality of staples 36 positioned in a disposable cartridge while the handle assembly 40 is configured to be reused with multiple staple cartridges. In the illustrated embodiment, the elongate shaft 20 and jaw assembly 30 define a disposable cartridge that is removably couplable to the handle assembly 40. Accordingly, in the illustrated embodiment the handle assembly 40 includes a coupler 46 at the distal end thereof. The coupler 46 is adapted to engage the elongate shaft 20 of the surgical stapler 10 The coupler 46 can have a bayonet connection having an outer connector that can removably couple the handle assembly 40 to the elongate shaft 20, and an inner connector that can removably couple the actuation shaft of the handle assembly 42 to the actuation member of the elongate shaft 20. Accordingly, the surgical stapler 10 can be configured such that the handle assembly 40 can be reused with multiple disposable cartridges during a surgical procedure. It is contemplated that in other embodiments, the handle assembly and some portion of the elongate shaft can be reusable while a remainder of the elongate shaft and the jaw assembly define a disposable cartridge. In certain other embodiments, the handle assembly and the elongate shaft can be reusable while the jaw assembly defines a disposable cartridge. In still other embodiments, a jaw insert housing a plurality of staples can define a disposable cartridge while the remainder of the surgical stapler is reasonable.

Figure 3:
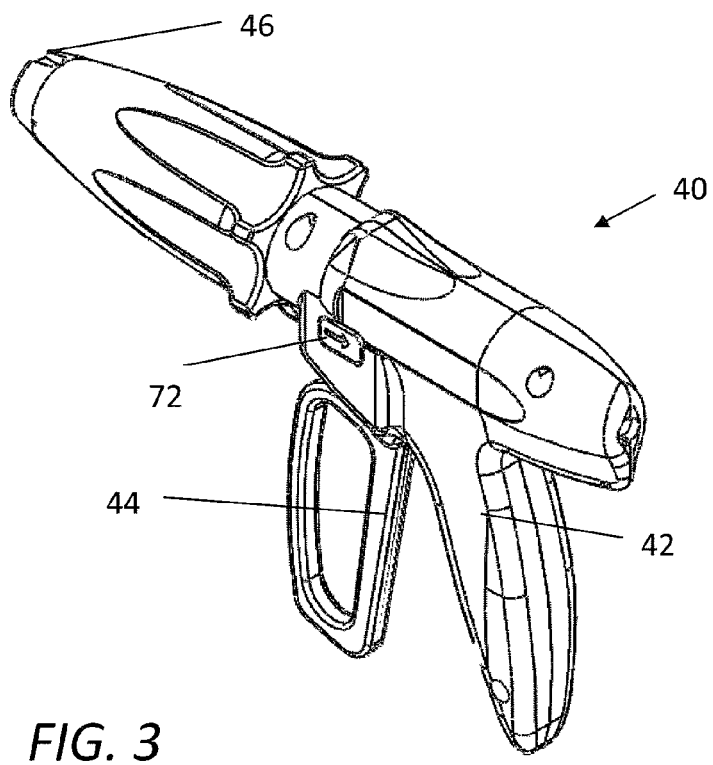
FIG. 3 is a perspective view of an embodiment of handle assembly for a surgical stapling device.

FIGS. 3-7 illustrate various views of an embodiment of handle assembly 40 for a surgical stapler 10. In FIG. 3, a perspective view of the handle assembly 40 as illustrated with the movable handle 44 in an open position spaced apart from the stationary handle 42. The illustrated handle assembly 40 further comprises a selector 72 operably coupled to the actuation mechanism housed within the handle assembly 40 as further discussed herein. As illustrated in FIG. 3, the selector 72 is in a first position.

Figure 4:
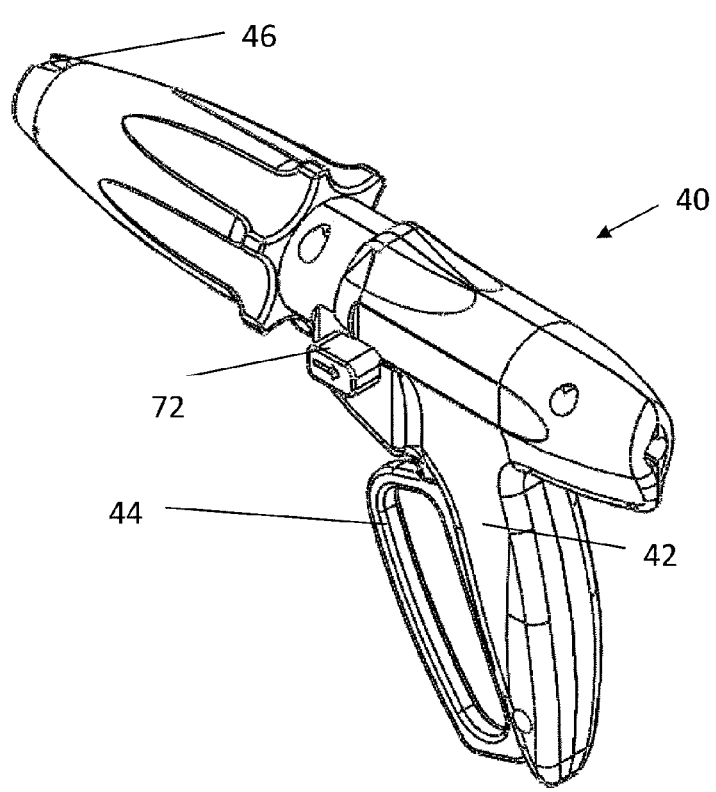
FIG. 4 is a perspective view of the handle assembly of FIG. 3 with a movable handle in a closed configuration.
Figure 5:
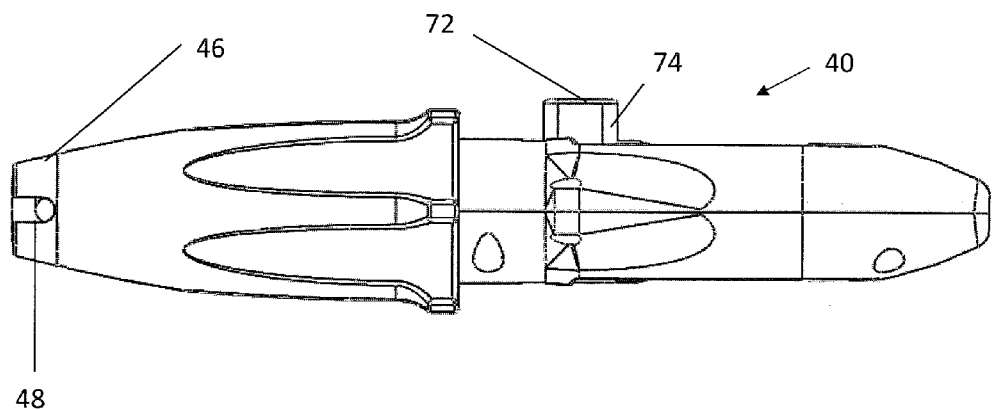
FIG. 5 is a top view of the handle assembly of FIG. 3 with a selector in a first configuration.
Figure 6:
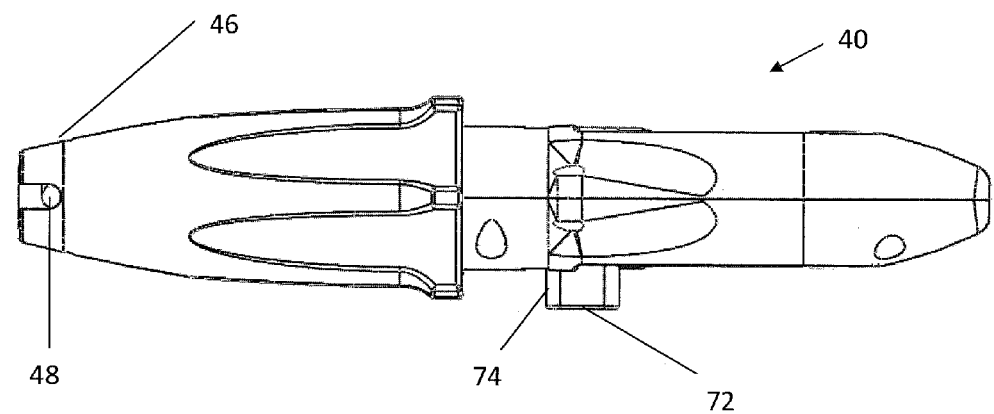
FIG. 6 is a top view of the handle assembly of FIG. 3 with a selector in a second configuration.
Figure 7:
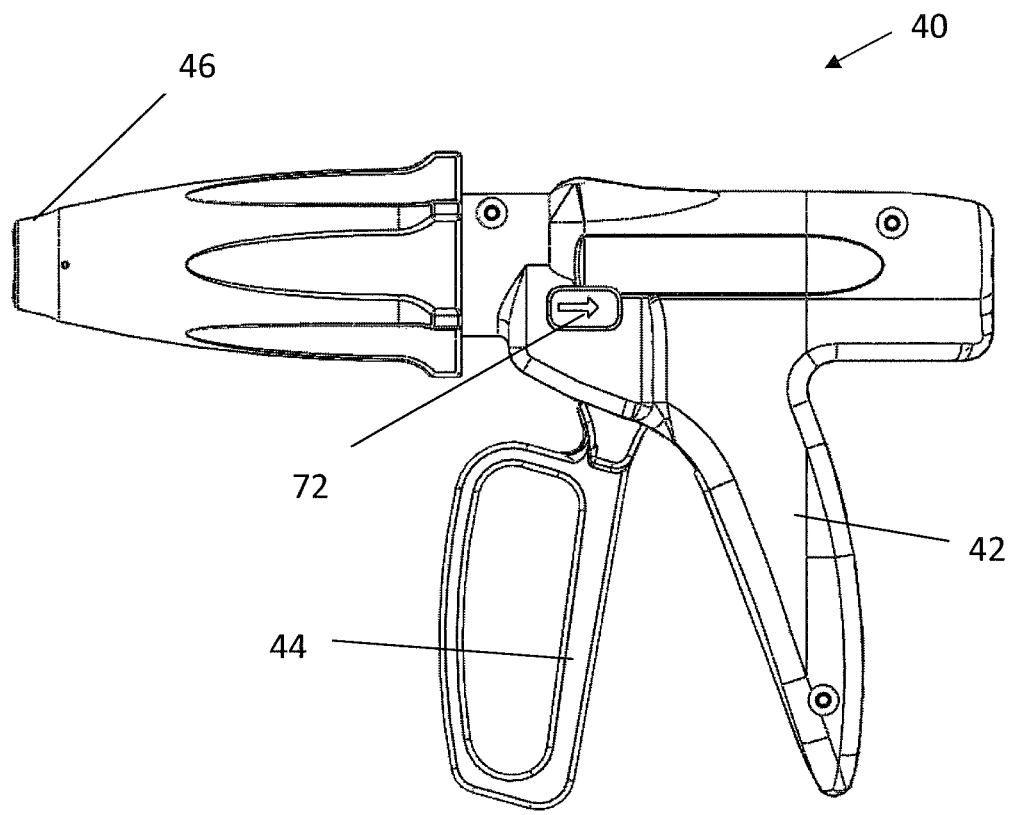
FIG. 7 is a side view of the handle assembly of FIG. 3.

With reference to FIG. 4, another perspective view of the handle assembly 40 of FIG. 3 is illustrated. As illustrated, the movable handle 44 is in a closed position positioned adjacent the stationary handle 42, and the selector 72 is in a second position. FIGS. 5 and 6 illustrate a top view of the handle assembly of FIG. 3 with the selector 72, such as a slider 74, in the first position (FIG. 5), and in the second position (FIG. 6). FIG. 7 illustrates a side view of the handle assembly 40 of FIG. 3.

Figure 8A:
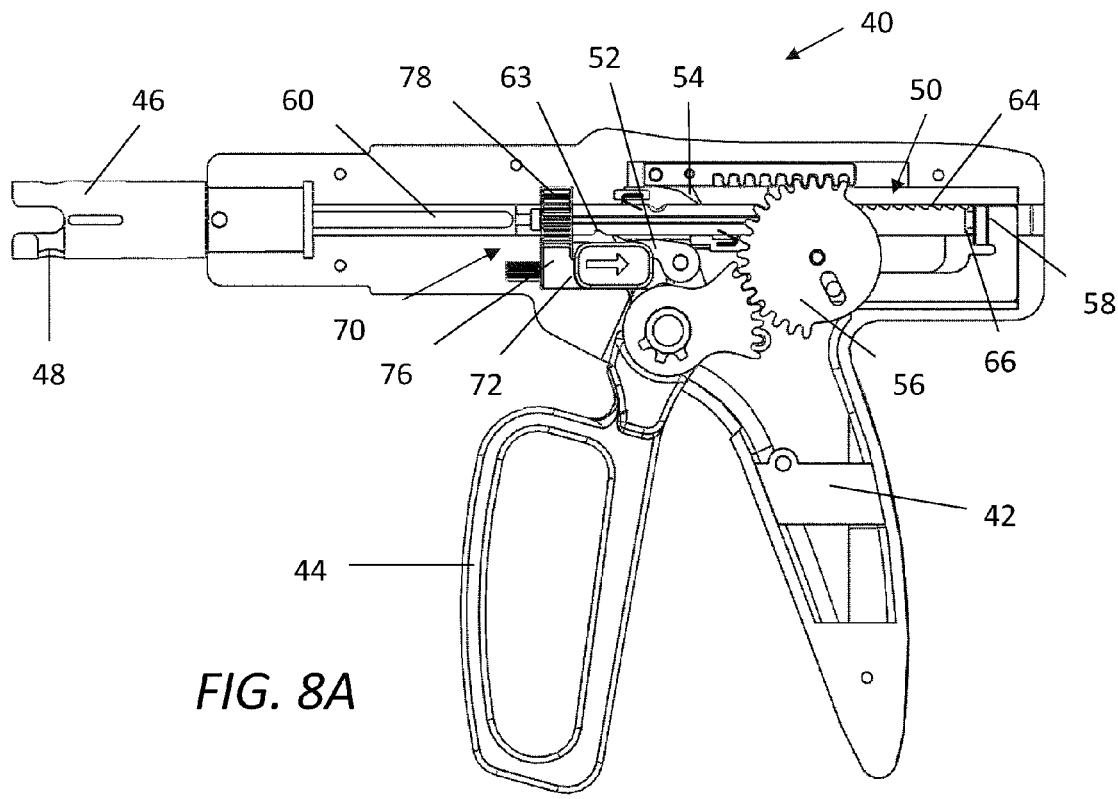
FIG. 8A is a cross-sectional side view of the handle assembly of FIG. 3 in an initial configuration.
Figure 8B:
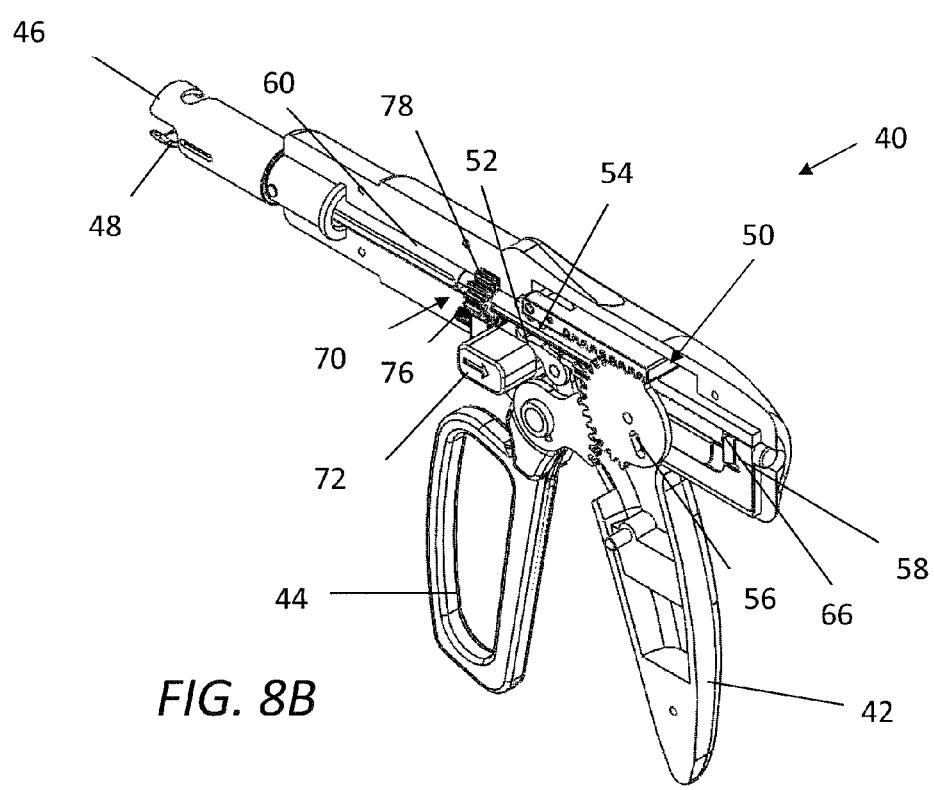
FIG. 8B is a cross-sectional perspective view of the handle assembly of FIG. 8A.

FIGS. 8A and 8B illustrate cross-sectional views of the handle assembly 40 in an initial configuration, revealing operation of the actuation mechanism 50. In the illustrated embodiment, the actuation mechanism 50 is configured to selectively translate the actuation shaft 60 from a first position corresponding to the jaw assembly 30 being in the open configuration to a second position corresponding to the jaw assembly 30 being in the closed configuration and from the second position to a third position to position the jaw assembly 30 in a stapling configuration and deploy the plurality of staples 36. In the initial configuration illustrated in FIGS. 8A and 8B, actuation mechanism 50 can repeatedly translate the actuation shaft 60 between the first position and the second position responsive to movement of the movable handle 44 or trigger without deploying the staples to provide an open and close functionality. This open and close functionality allows a user to position, clamp tissue, and reposition the stapler 10 to find a desirable staple placement location before deploying the staples.

With reference to FIGS. 8-14, in the illustrated embodiment, the actuation mechanism comprises an advancing or forward driver 52, a reverse driver 54, a opening driver 58, an advancing surface 62, a reversing surface 64, and a opening surface 66. The forward driver 52 can be operably coupled to the movable handle 44 such that movement of the movable handle 44 from the open position to the closed position advances the forward driver 52 in a first direction such as for example distally within the handle assembly 40. The forward driver 52 can comprise a pawl or tooth configured to engage a recess or slot.

The reverse driver 54 can be operably coupled to movable handle 44 such that movement of the movable handle 44 from the open position to the closed position advances the reverse driver 54 in a second direction opposite the first direction such as, for example proximally within the handle assembly 40. In some embodiments, the movable handle 44 can be operably coupled with the reverse driver 54 with a geared connection including an idler gear 56. The reverse driver 54 can comprise a pawl or tooth configured to engage a recess or slot.

The opening driver 58 can be operably coupled to the movable handle 44 such that movement of the movable handle 44 from the open position to the closed position advances the opening driver 58 in a first direction such as for example distally within the handle assembly 40. In the illustrated embodiment, the opening driver 58 is coupled to the idler 56 with a pin and slot connection to operably couple the opening driver 58 to the movable handle 44. The opening driver 58 can comprise a pawl or tooth configured to engage a recess or slot.

The actuation shaft 60 includes advancing surface 62, reversing surface 64, and opening surface 66 formed thereon. In the illustrated embodiment, the advancing surface 62 comprises a rack, or plurality of spaced recesses or teeth formed longitudinally along the actuation shaft 60. As illustrated, reversing surface 64 comprises a rack or plurality of space recesses or teeth formed longitudinally along the actuation shaft 60 and angularly offset from the advancing surface 62. In the illustrated embodiment, the opening surface 66 comprises a recess formed in the actuation shaft 60.

In certain embodiments, the actuation shaft 60 is rotatable within the handle assembly 40 about the longitudinal axis of the stapler 10. The handle assembly 40 can comprise a rotation mechanism 70 to provide selective rotation of the actuation shaft 60 within the handle assembly 40. The actuation shaft 60 can be rotatable between a first orientation in which the forward driver 52 is engageable with the advancing surface 62 and a second orientation in which the reverse driver 54 is engageable with the reversing surface 64. With the angular offset of the advancing surface 52 from the reversing surface 54 with respect to the actuation shaft 60, with the actuation shaft in the first orientation, the reverse driver 54 is disengaged from the reversing surface 64, and with the actuation shaft in the second orientation, the forward driver 52 is disengaged from the advancing surface 62.

With continued reference to FIGS. 8-14, in certain embodiments, the rotation mechanism 70 comprises a selector 72, such as a slider. The slider can extend transversely through the housing of the handle assembly 40. The slider can be operably coupled to the actuation shaft 60 such that positioning the slider in the first position extending from one side of the handle assembly 40 positions the actuation shaft 60 in the first orientation, and positioning the slider in the second position extending from an opposite side of the handle assembly 40 rotates the actuation shaft 60 to the second orientation. In the illustrated embodiment, the slider is coupled to a rack 76 in meshing engagement with a gear 78 that is rotatably fixed to the actuation shaft 60 and longitudinally slidable along the actuation shaft 60 (such as, for example, with a keyed connection). Desirably, the illustrated rotation mechanism 70 including a slider discretely positions the actuation shaft 60 in a desired orientation, reducing the incidence of the mismeshed gearing within the actuation mechanism 50. In some embodiments the slider can include visual indicators, such as arrows, to indicate the orientation of the actuation shaft 60, and thus, the actuation mode of the stapler to a user.

In the illustrated embodiment, the advancing surface 62 and the reverse surface 64 are angularly offset by approximately 90 degrees about the actuation shaft. Thus, the rotation mechanism 70 is configured to rotate the actuation shaft approximately 90 degrees between the first orientation and the second orientation. In other embodiments, the actuation surface 62 and the reverse surface 64 can have a different angular offset, such as, for example 120 degrees, and the rotation mechanism 70 can be configured to rotate the actuation shaft 60 correspondingly. Moreover, as described in further detail herein with respect to an open/close mode of the handle assembly 40 operation, in the illustrated embodiment, the opening driver 58 engages with the actuation shaft in the second orientation, in other embodiments, the actuation shaft can be rotatable to a third orientation in which the opening driver 58 engages with the actuation shaft.

With reference to FIGS. 8-14, a typical operation sequence of the actuation mechanism 50 of the handle assembly 40 is illustrated. FIGS. 8A-8B and 9A-9B illustrate operation of the handle assembly 40 in an initial configuration providing an open/close functionality to the jaw assembly 30. In FIG. 8A, the movable trigger 44 is at an open position, and the actuation shaft 60 is at a first position, corresponding to the first position of the actuation beam at the distal end of the elongate shaft 20. In the initial position, the actuation shaft 60 is positioned at the second orientation such that the reverse driver 54 is angularly aligned with the reversing surface 64. With actuation shaft 60 in the second orientation, the opening driver 58 is positioned within the opening surface 66 or recess. Movement of the movable handle 44 from the open position (FIG. 8A-8B) to the closed position (FIG. 9A-9B), advances the forward driver 52 distally along the actuation shaft 60 to engage an advancing recess 63 formed in the actuation shaft 60 and drive the actuation shaft 60 distally in the handle assembly 40 to a second position. The second position of the actuation shaft 60 within the handle assembly 40 corresponds to the second position of the actuation beam, which positions the jaw assembly 30 in a closed configuration.

Figure 11A:
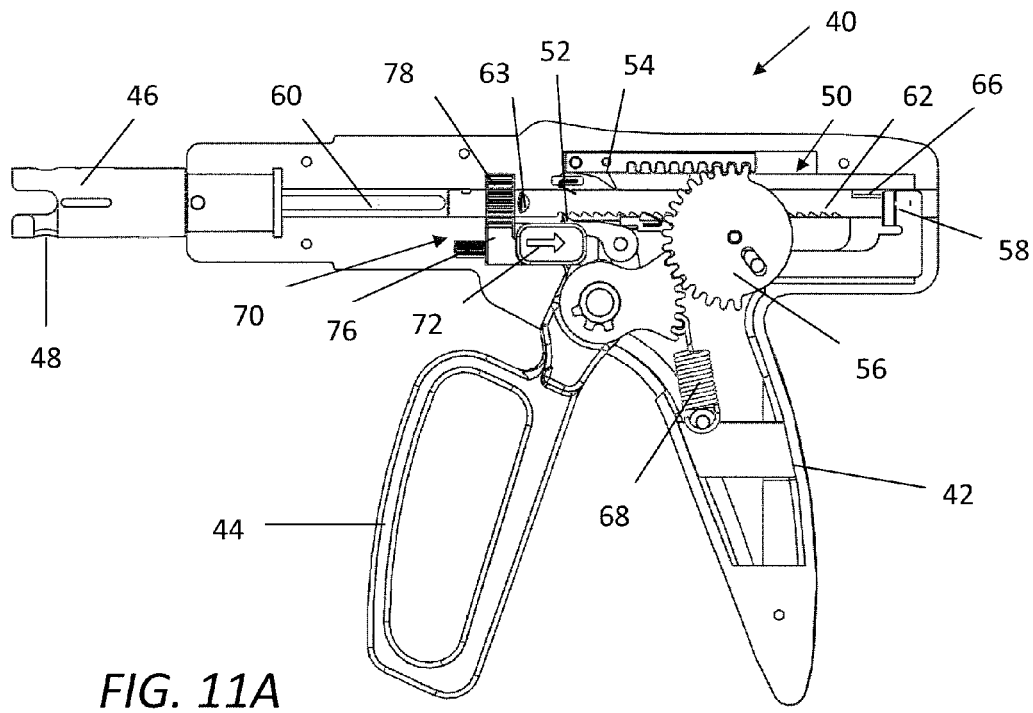
FIG. 11A is a cross-sectional side view of the handle assembly of FIG. 3 in the forward drive configuration.
Figure 11B:
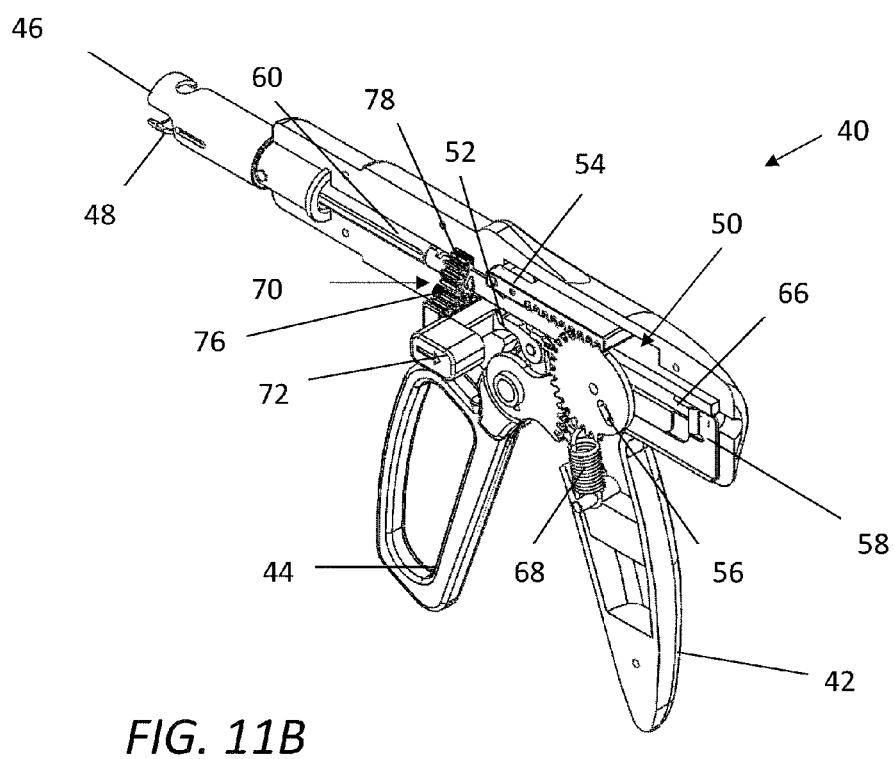
FIG. 11B is a cross-sectional perspective view of the handle assembly of FIG. 11A.

The movable handle 44 can be biased to the open position by a biasing member, such as a coil spring 68 (FIG. 11A).

Figure 9A:
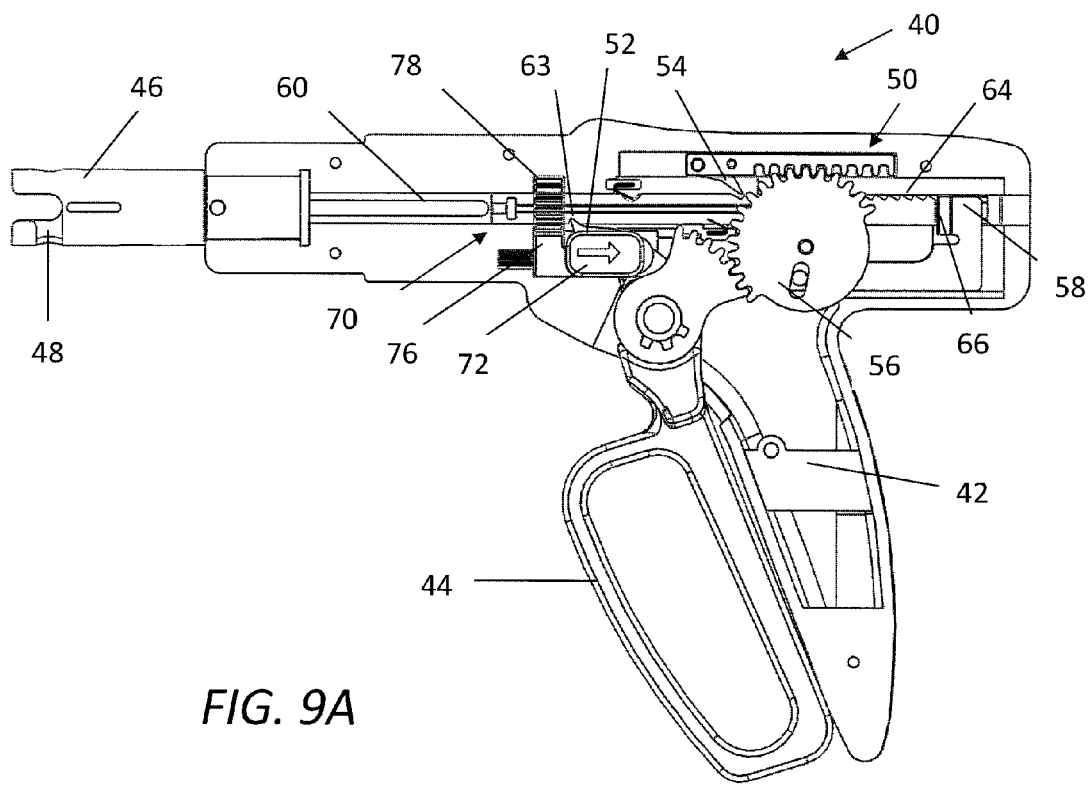
FIG. 9A is a cross-sectional side view of the handle assembly of FIG. 3 actuated to a closed configuration.
Figure 9B:
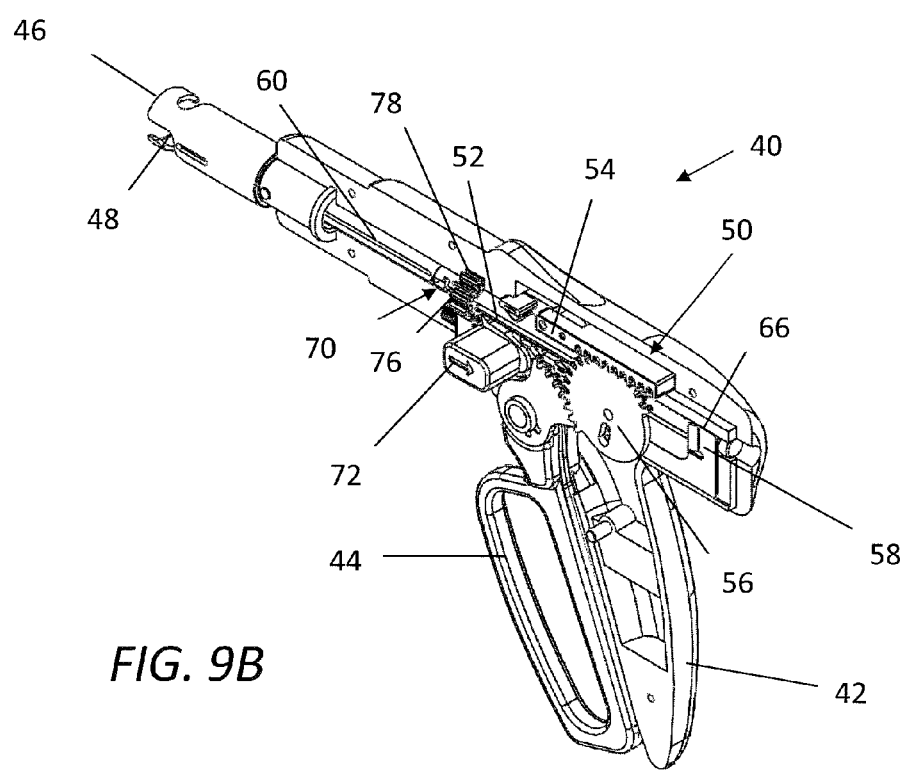
FIG. 9B is a cross-sectional perspective view of the handle assembly of FIG. 9A.

Thus, releasing the movable handle 44 from the closed position illustrated in FIG. 9A-9B would return it to the open position of FIGS. 8A-8B. Operable coupling of the movable handle 44 to the opening driver 58 would likewise translate the opening driver 58 proximally within the handle assembly 40 as the movable handle 44 returns to the open position. In the second orientation of the actuation shaft 60, the opening driver 58 engages opening surface 66 such that the proximal movement of the opening driver 58 returns the actuation shaft 60 from the second position to the first position, returning the jaw assembly 30 to the open configuration.

Figure 10A:
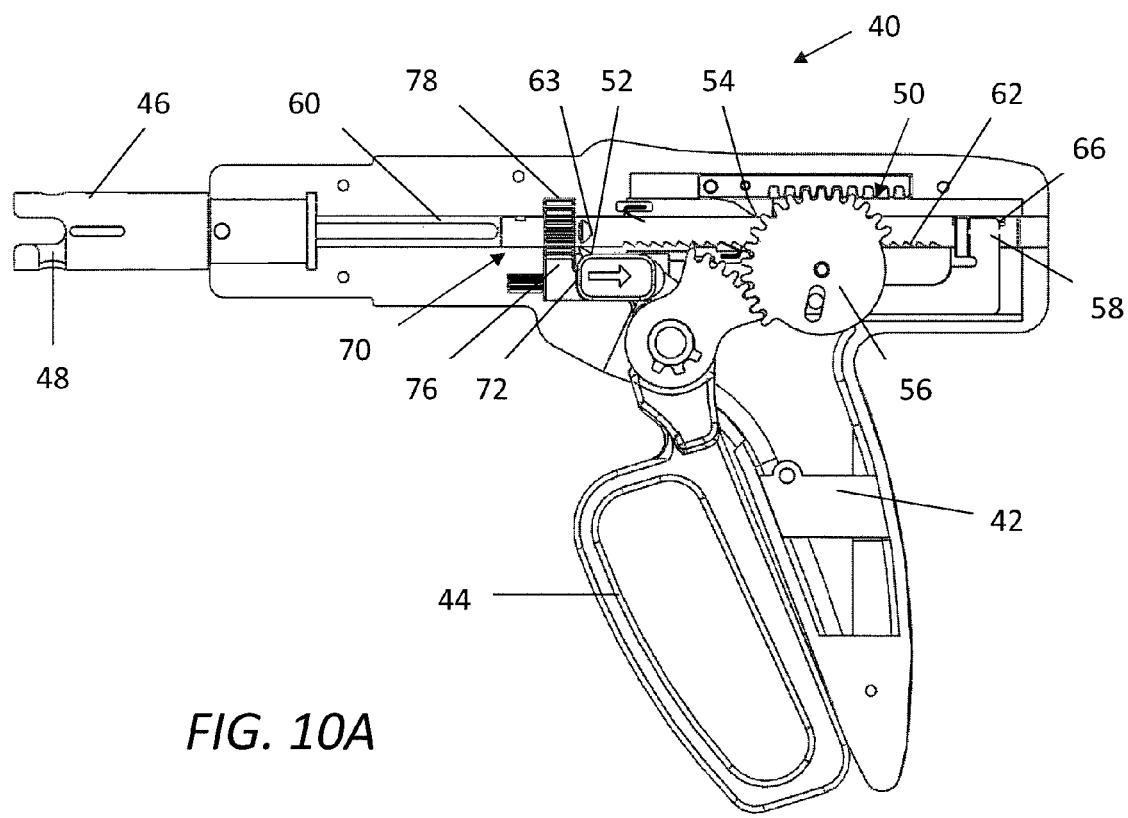
FIG. 10A is a cross-sectional side view of the handle assembly of FIG. 3 in a forward drive configuration.
Figure 10B:
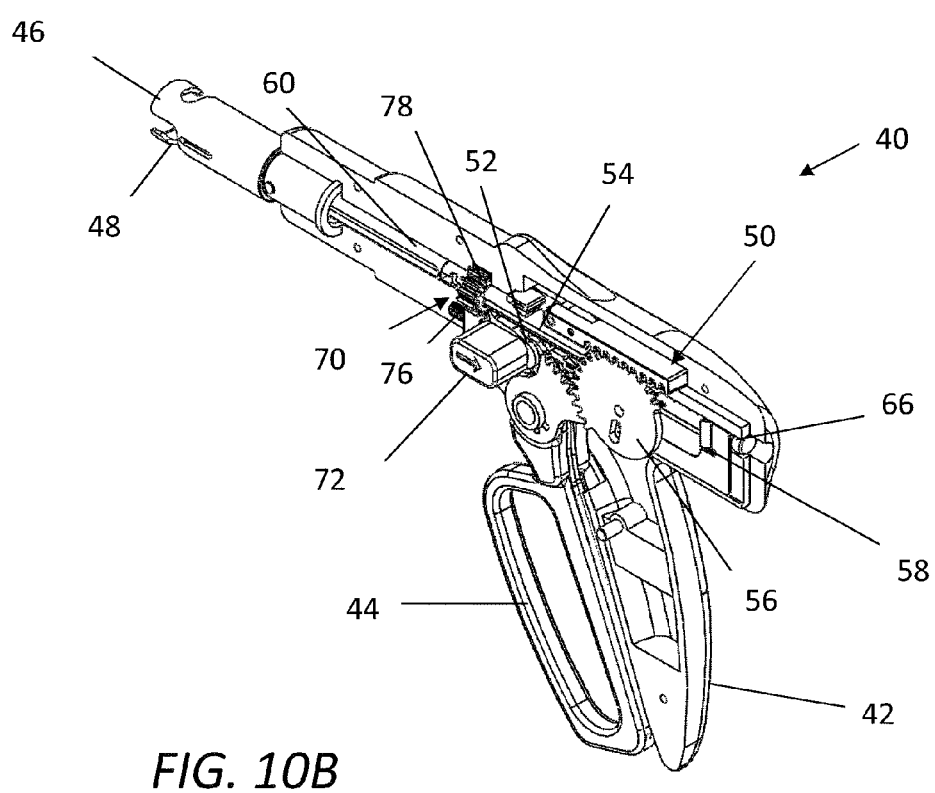
FIG. 10B is a cross-sectional perspective view of the handle assembly of FIG. 10A.

A user can seek a desired stapling position within a surgical field by repeatedly opening and closing the jaws to clamp tissue in various locations. Once a desired stapling position has been selected, the actuation mechanism 50 can be configured in a stapling or firing mode by rotating the actuation shaft 60 to the first orientation. With the jaw assembly a closed configuration at a desired stapling position (as illustrated in FIGS. 9A-9B), a user can reposition the selector 72 by sliding the slider to the first position, corresponding to the first orientation of the actuation shaft 60 (as illustrated in FIGS. 10A-10B). In the first orientation of the actuation shaft 60, the forward driver 52 is engageable with the advancing surface 62, the reversing driver 54 is angularly misaligned with the reversing surface 64, and the opening driver 58 angularly misaligned with the opening surface 66. With the actuation shaft 60 in the first orientation, the movable handle 44 can be released into the open position (FIG. 11A-11B), engaging the forward driver 52 with the advancing surface 62.

Figure 12A:
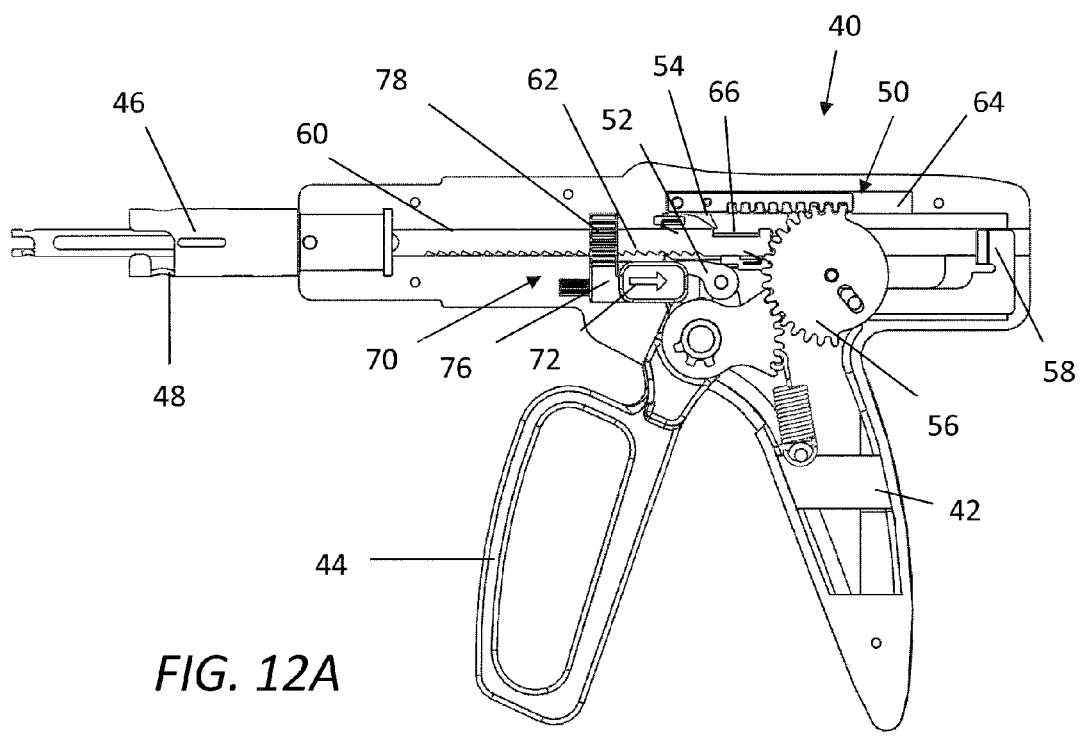
FIG. 12A is a cross-sectional side view of handle assembly of FIG. 3 in a fully driven forward configuration.
Figure 12B:
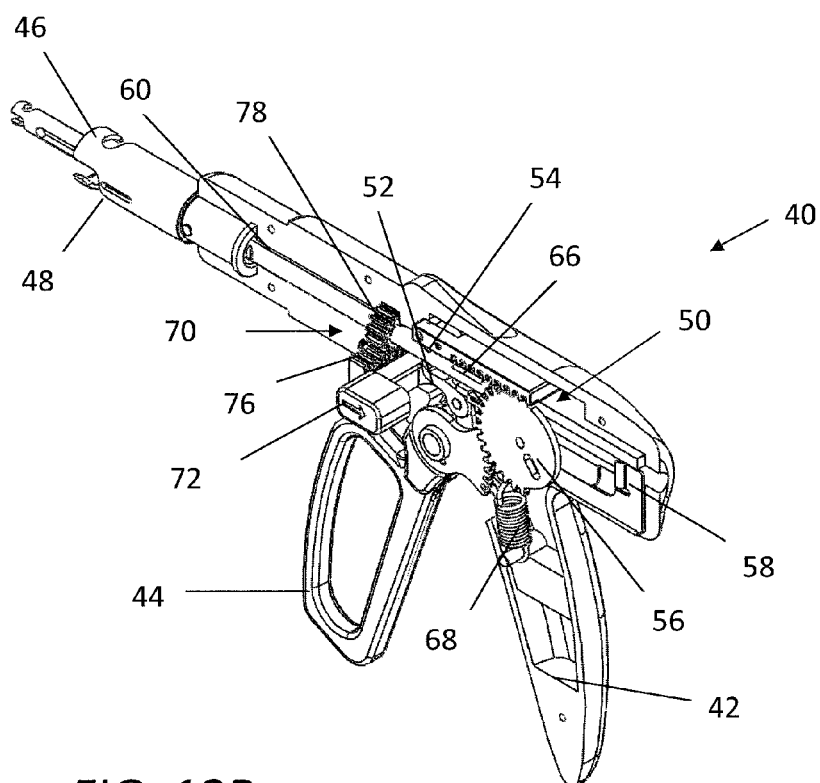
FIG. 12B is a cross-sectional perspective view of the handle assembly of FIG. 12A.

With reference to FIGS. 11A-11B and 12A-12B, with the actuation shaft 60 in the first orientation, and the forward driver 52 engaging the advancing surface 62, the actuation mechanism 50 is in a stapling or firing mode. Several cycles of movable handle 44 movement from the open position to the closed position and back to the open position advance the actuation shaft 60 from the second position (FIGS. 11A-11B), to a third position in which the actuation shaft 60 is moved to its distal-most limit with respect to the handle assembly 40 (FIGS. 12A-12B). In some embodiments, the actuation mechanism can include a stop to interfere with distal travel of the actuation shaft 60 at the third position. The second position of the actuation shaft corresponds to the second position of the actuation beam in the jaw assembly 30. The third position of the actuation shaft corresponds to the third position of the actuation beam in the jaw assembly 30 in which the plurality of staples have been deployed from the first jaw. With movement of the movable handle 44 or trigger in the firing mode to advance the actuation shaft from the second position to the third position, the forward driver 52 is sequentially advanced over the adjacent teeth or grooves of the actuating surface 62 in a ratchet-like advancement.

Figure 13A:
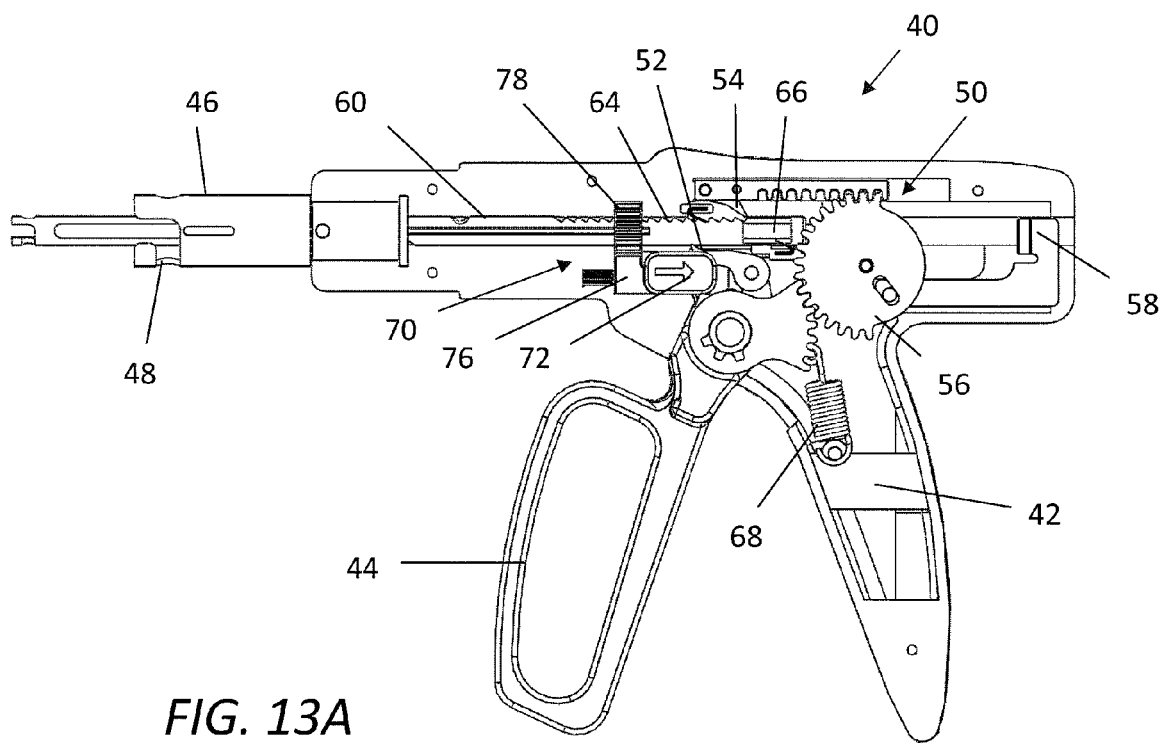
FIG. 13A is a cross-sectional side view of the handle assembly of FIG. 3 in a reverse drive configuration.
Figure 13B:
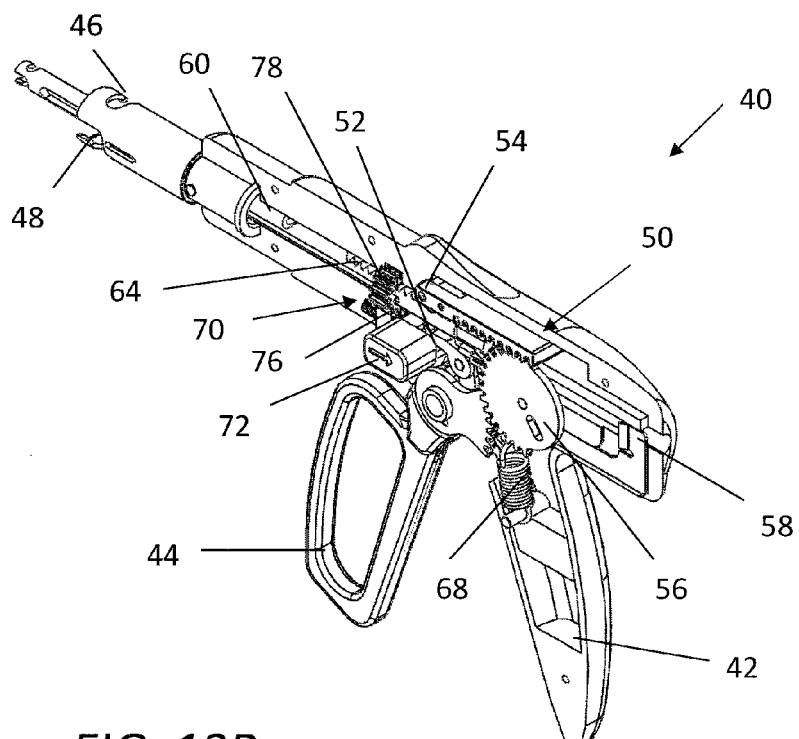
FIG. 13B is a cross-sectional perspective view of the handle assembly of FIG. 13A.
Figure 14A:
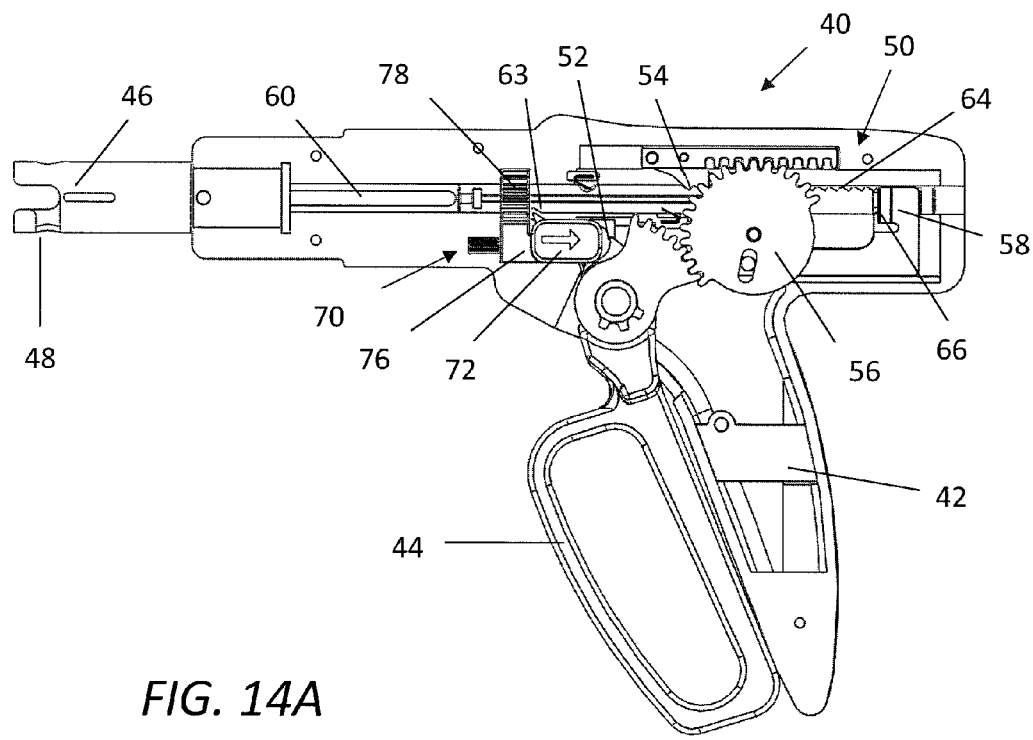
FIG. 14A is a cross-sectional side view of the handle assembly of FIG. 3 in a fully driven reverse configuration.
Figure 14B:
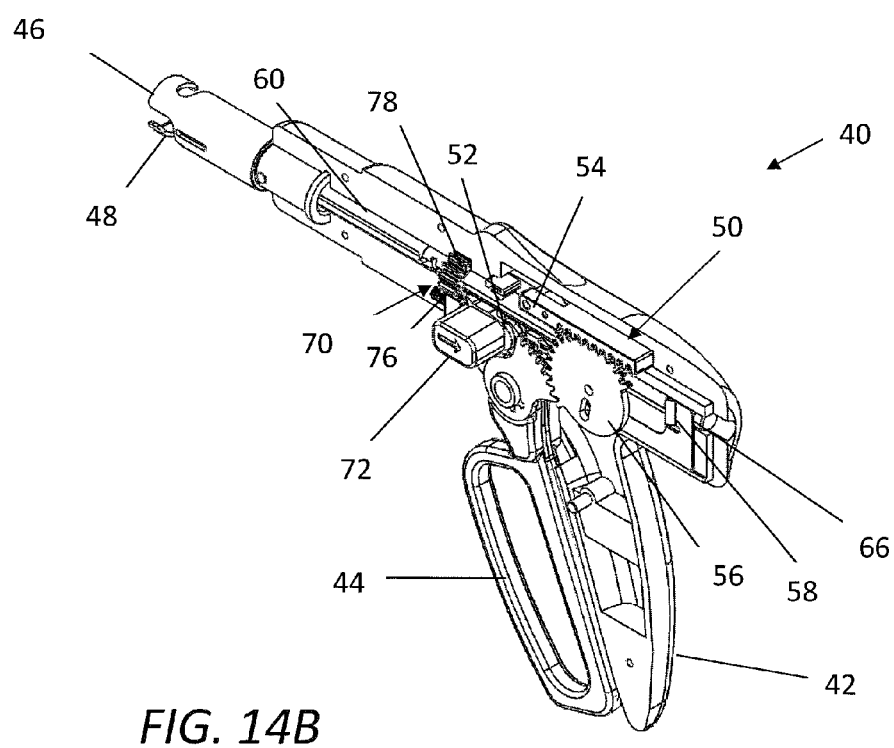
FIG. 14B is a cross-sectional perspective view of the handle assembly of FIG. 14A.

With reference to FIGS. 13A-13B, once the actuation shaft 60 has been advanced to the third position and the staples have been fired from the jaw assembly, the actuation mechanism 50 can be configured in a reverse mode. Accordingly, the rotation mechanism 70 can rotate the actuation shaft 60 to the second orientation to position the reversing surface 64 in angular alignment with the reverse driver 54. The slider can be slid to the second position to rotate the actuation shaft from the first orientation (FIGS. 12A-12B) to the second orientation (FIGS. 13A-13B). With the actuation shaft 60 in the second orientation, repeated cycles of the movable handle 44 from the open position to the closed position and back to the open position engage the reverse driver 54 with the reversing surface 64 in a ratchet-like advancement while retracting the actuation shaft 60 proximally in the handle assembly 40. Once the reverse driver 54 has driven the actuation shaft 60 proximally to the second position (illustrated in FIGS. 14A-14B), the opening driver 58 engages the opening surface 66. The opening driver 58 returns the actuation shaft 60 to the first position when the movable handle 44 is released to the open position. (Returning the handle assembly to the configuration illustrated in FIGS. 8A-8B). With the actuation shaft 60 in the first position, the cartridge, emptied of staples, can be decoupled from the handle assembly 40 and a new cartridge can be coupled to the handle assembly to begin another stapling operation.

Figure 15:
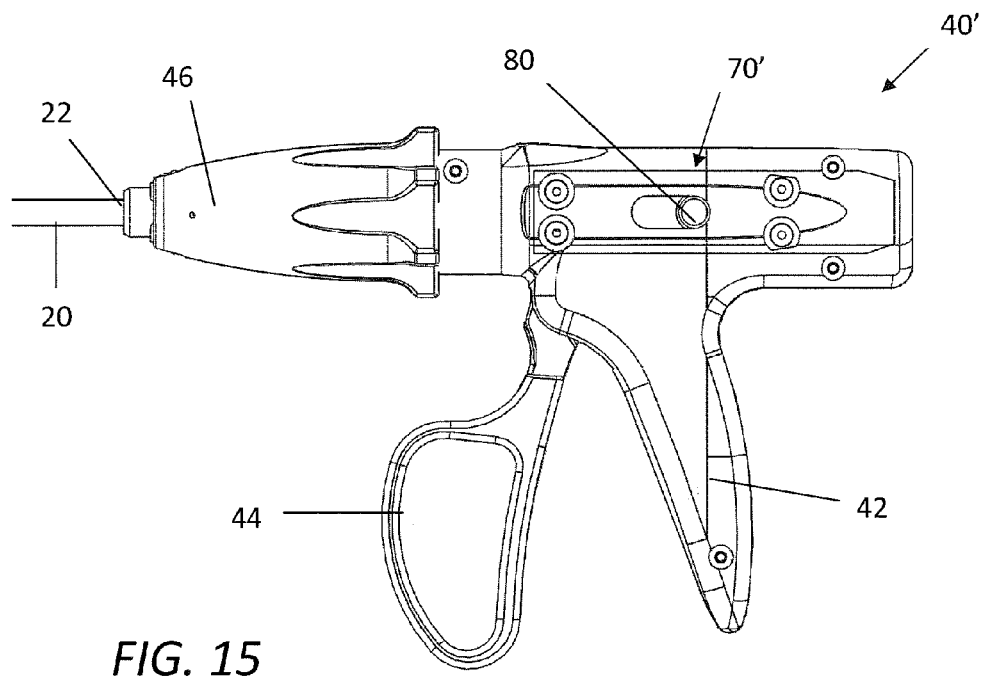
FIG. 15 is a side view of another embodiment of handle assembly for a surgical stapling device.
Figure 16:
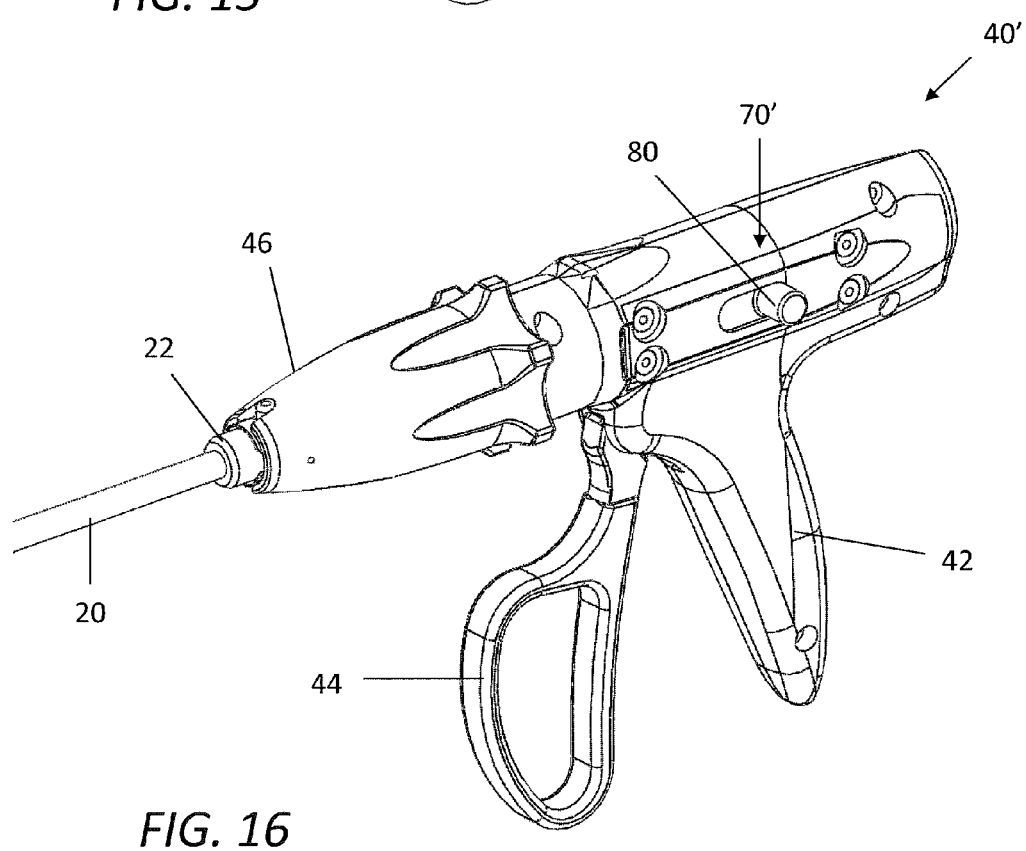
FIG. 16 is a perspective view of the handle assembly of FIG. 15.

With reference to FIGS. 15-25, another embodiment of handle assembly 40' for use with a surgical stapler 10' is illustrated. FIG. 15 illustrates a side view of the handle assembly 40', and FIG. 16 illustrates a perspective view of the handle assembly 40'. In the handle assembly 40', actuation of the rotation mechanism 70' is accomplished with a slidable switch 80 that is longitudinally slidable with respect to the handle assembly 40' housing. Advantageously, such a slidable switch arrangement can allow a user to easily rotate the actuation shaft 60 in a single-handed operation.

Figure 17:
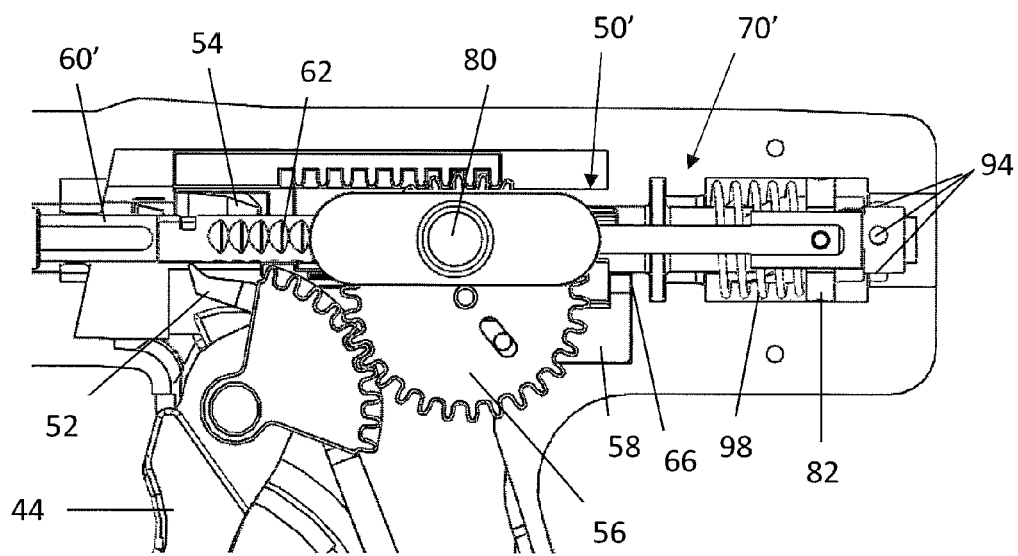
FIG. 17 is a cutaway side view of the handle assembly of FIG. 15.

With reference to FIG. 17, a cross-sectional view of the handle assembly 40' is illustrated revealing the actuation mechanism 50' and the rotation mechanism 70'. The actuation mechanism functions substantially as described above with respect to the embodiment of FIGS. 8A,8B-14A,14B to advance the actuation shaft 60' from a first position to a second position in an open/close mode, from the second position to a third position in a stapling mode, and from the third position to the first position in a reverse mode. The actuation mechanism 50' includes corresponding forward, reverse, and opening drivers 52, 54, 58 operably coupled to a movable handle 44 and advancing 62, reversing, and opening surfaces on the actuation shaft 60' substantially as described with respect to the embodiment of FIGS. 8A,8B-14A-14B. However, in the embodiment illustrated in FIGS. 15-25, the actuation shaft 60' is rotatable by the rotation mechanism 70' discretely between a first orientation corresponding to the open/close mode of the handle assembly wherein the opening driver 58 engages the opening surface 66, a second orientation corresponding to the stapling position, wherein the forward driver 52 engages the advancing surface 62, and a third orientation corresponding to the reverse position wherein the reverse driver 54 engages the reversing surface.

Figure 18:
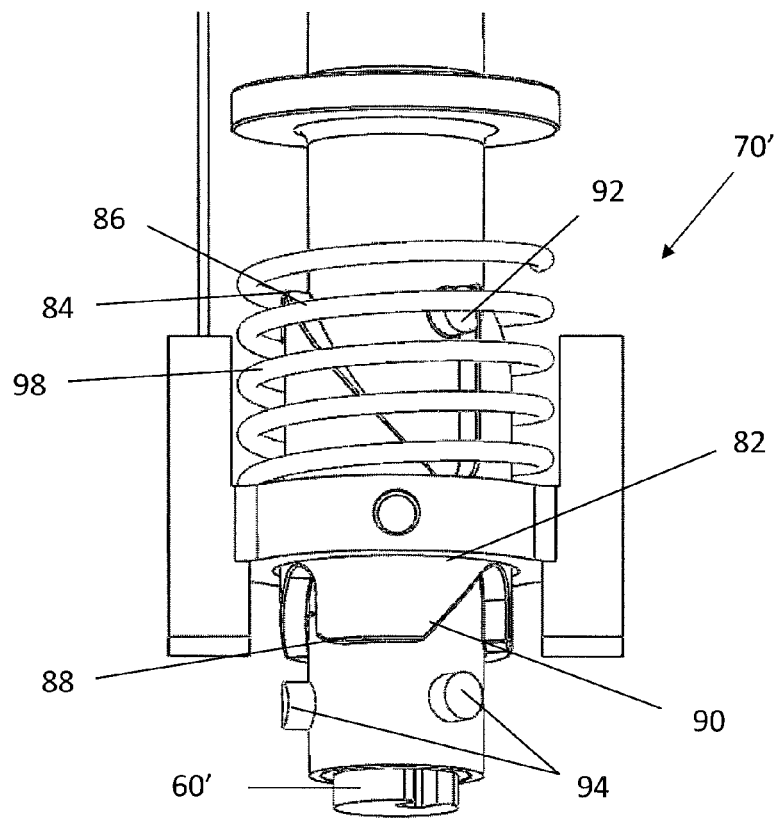
FIG. 18 is a top view of a rotation mechanism for an actuation mechanism of the handle assembly of FIG. 15.

With reference to FIGS. 17-18, certain aspects of the rotation mechanism 70' are illustrated. The rotation mechanism 70' comprises the slidable switch 80 longitudinally slidable with respect to the housing of the handle assembly 40', a hub collar 82 longitudinally slidable by the switch 80, and a biasing member or spring 98. In the illustrated embodiment, the slidable switch 80 is connected to the hub collar 82 with a thin beam, such as a shim member. The hub collar 82 is rotationally fixed and longitudinally slidable with respect to the housing of the handle assembly 40'. In some embodiments, the hub collar 82 can comprise first and second wings that can slide in corresponding first and second slots in the housing of the handle assembly to allow relative longitudinal movement and restrict relative rotational movement therebetween.

The hub collar 82 can be a generally tubular member disposed around the actuation shaft 60'. The hub collar 82 can extend between a first edge 84 having a plurality of ramps 86 formed therein and a second edge 88 having a plurality of recesses 90 formed therein. In the illustrated embodiment, the hub collar 82 comprises three ramps 86 formed in the first edge 84 with each ramp spaced approximately 120 degrees apart from adjacent ramps 86. As illustrated, the hub collar 82 comprises three recesses 90 formed in the second edge 88 with each recess 90 being approximately 120 degrees apart from adjacent recesses 86. In other embodiments, the number and relative spacing of ramps 86 and recesses 90 can vary to rotate the actuation shaft 50 between different orientations from those of the illustrated embodiment.

In some embodiments, the rotation mechanism 70' can include a spring 98 to bias the slidable switch 80 and the hub collar 82 to a proximal position with respect to the housing of the handle assembly 40'.

With continued reference to FIGS. 17-18, the actuation shaft 60' can have a first plurality of projections 92 projecting radially outwardly therefrom adjacent the first edge 84 of the hub collar 82. In the illustrated embodiment, the actuation shaft has three projections 92 each spaced approximately 120 degrees from the adjacent projections. The actuation shaft 60' can further comprise a second plurality of projections 94 extending radially outwardly from the actuation shaft 60' at a position adjacent the second edge 88 of the hub collar 82. In the illustrated embodiment, the actuation shaft 60' has three projections 94 each spaced approximately 120 degrees from the adjacent projections. In other embodiments, the numbers and spacing of the projections 92, 94 can be varied to achieve a rotation mechanism with different rotational characteristics. In some embodiments, the projections 92, 94 can be formed on the actuation shaft 60', while in other embodiments, the projections 92, 94 can be formed separately such as on a sleeve that is adhered to, has a keyed engagement with, or is otherwise rotationally fixed to the actuation shaft 60'.

Figure 19:
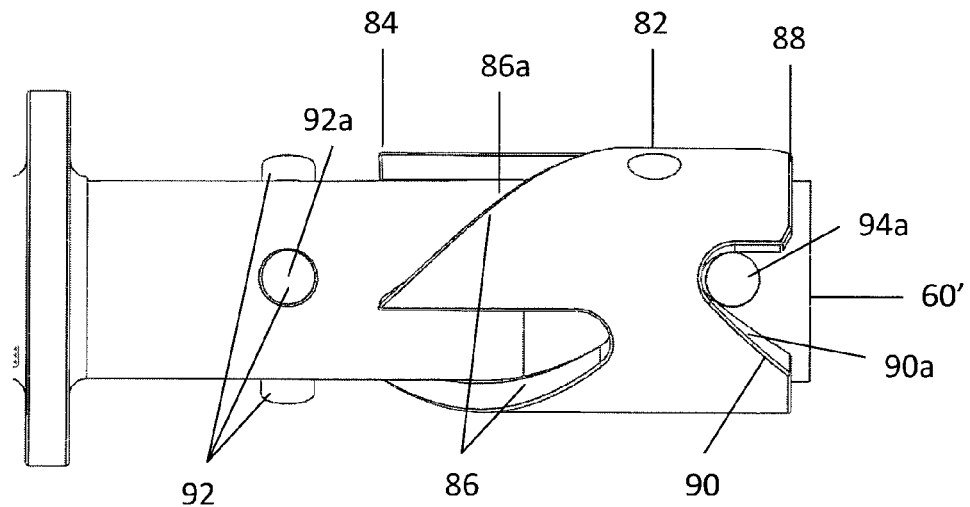
FIG. 19 is a top view of a hub collar and actuation shaft of the rotation mechanism of FIG. 18 with the hub collar in a first position.
Figure 20:
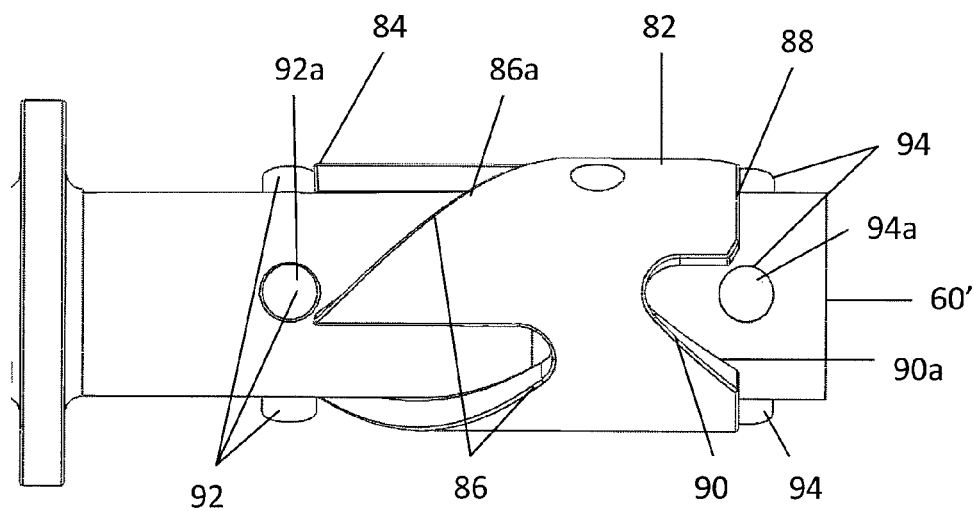
FIG. 20 is a top view of the hub collar and actuation shaft of the rotation mechanism of FIG. 18 with a hub collar in a second position.
Figure 21:
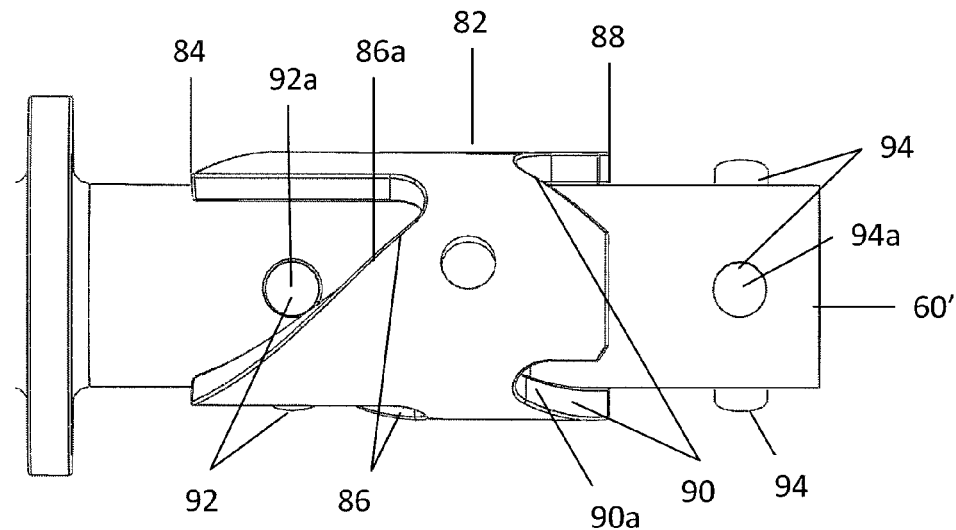
FIG. 21 is a top view of the hub collar and actuation shaft of the rotation mechanism of FIG. 18 with a hub collar in a third position.
Figure 22:
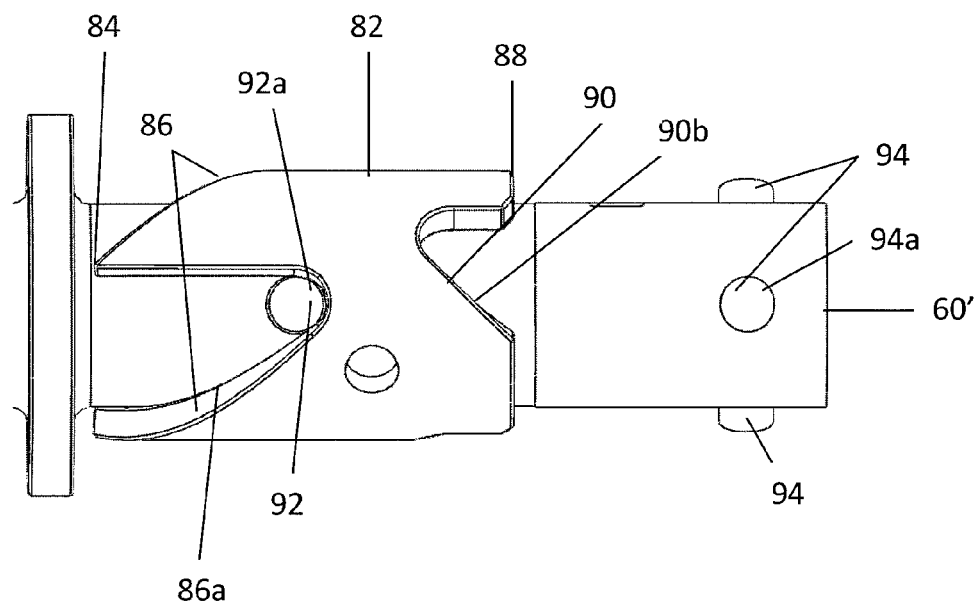
FIG. 22 is a top view of the hub collar and actuation shaft of the rotation mechanism of FIG. 18 with a hub collar in a fourth position.
Figure 23:
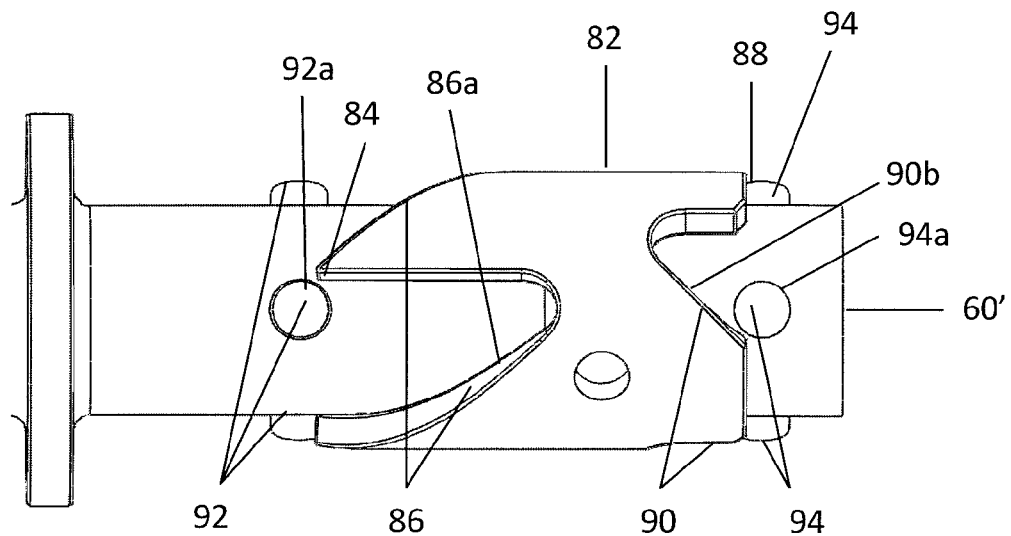
FIG. 23 is a top view of the hub collar and actuation shaft of the rotation mechanism of FIG. 18 with a hub collar in a fifth position.
Figure 24:
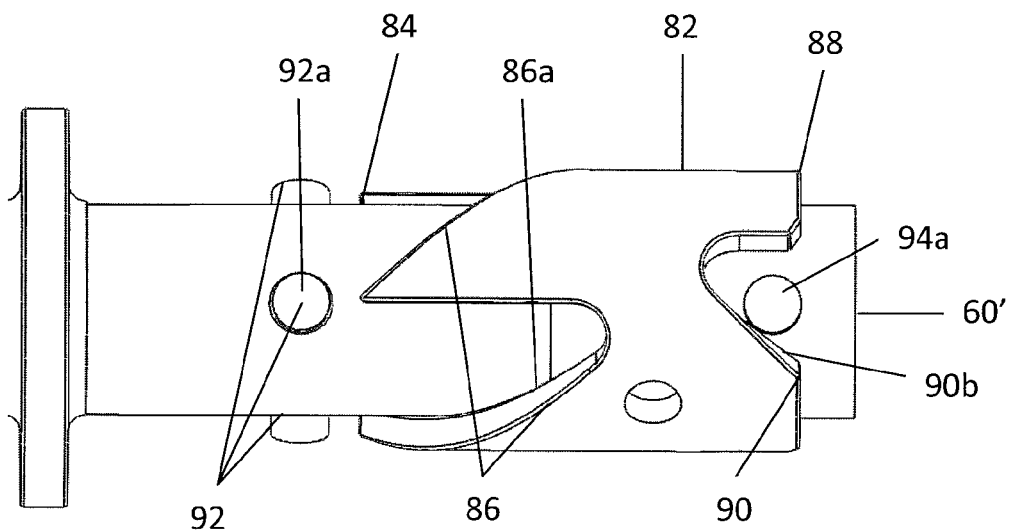
FIG. 24 is a top view of the hub collar and actuation shaft of the rotation mechanism of FIG. 18 with a hub collar in a sixth position.

With reference to FIGS. 19-25, an operation sequence of the rotation mechanism 70' to rotate the actuation shaft 60' from a first orientation to a second orientation is illustrated. FIG. 19 illustrates a schematic view of the hub collar 82 and actuation shaft 50' in a first orientation. In the first orientation, a first projection 94a of the second plurality of projections 94 rests in a first recess 90a of the plurality of recesses 90, and a first projection 92a of the first plurality of projections is positioned adjacent a first ramp 86a of the plurality of ramps 86.

Figure 25:
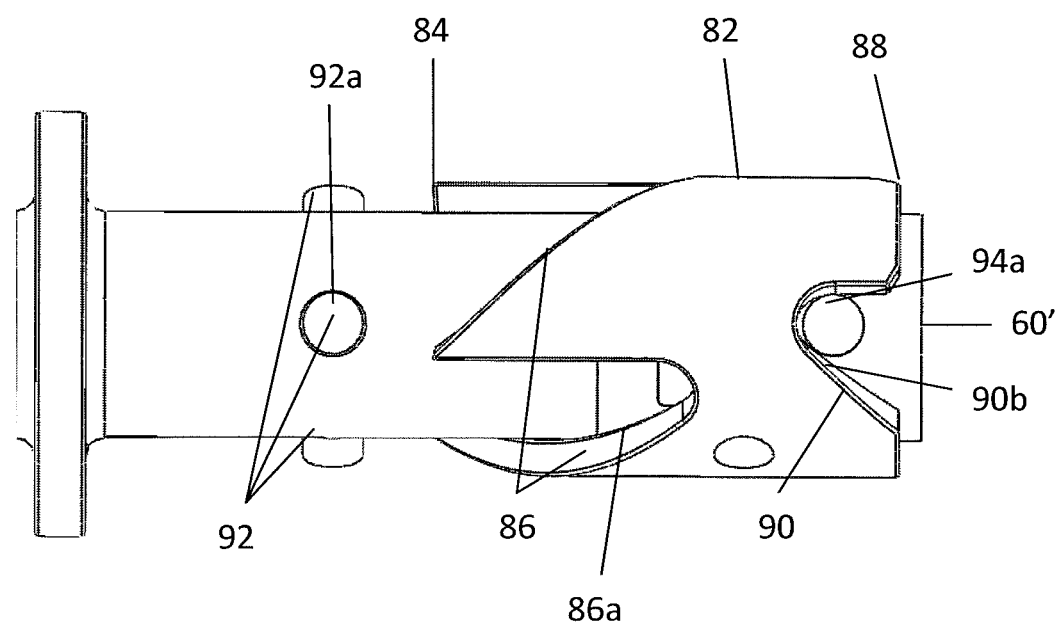
FIG. 25 is a top view of the hub collar and actuation shaft of the rotation mechanism of FIG. 18 with a hub collar in a seventh position.

With reference to FIGS. 19-22, an operation sequence of the rotation mechanism 70' as the slidable switch 80 is advanced distally is illustrated. As the slidable switch 80 is advanced distally with respect to the housing of the handle assembly, the hub collar 82 translates distally, bringing the first plurality of projections 92 into sliding engagement with the plurality of ramps 86 of the hub collar 82 (illustrated in FIG. 20). Further distal advancement of the slidable switch 80 and hub collar 82 relative to the housing of the handle assembly advances the first plurality of projections 92 over the plurality of ramps 86 (illustrated in FIGS. 21 and 22). An angular profile of the ramps 86 acts as a camming surface such that travel of the first plurality of projections 92 along the plurality of ramps 86 rotates the actuation shaft 60'. Once the slidable switch reaches the distal most end of its travel, the spring 98 biases the hub collar 82 and sliding switch 80 proximally with respect to the housing of the handle assembly 40. As the hub collar 82 returns to a proximal position, the second plurality of projections 94 engages the plurality of recesses 90 (illustrated in FIGS. 23-25). As illustrated in FIG. 25, following an actuation cycle of the slidable switch 80, the first projection 94a of the second plurality of projections 94 has been positioned in the second recess 90b of the plurality of recesses such that the actuation shaft 60' has been positioned in a second orientation rotated 120 degrees from the first orientation. Subsequent actuation cycles of the slidable switch 80 rotate the actuation shaft in discrete 120 degree increments.

In other embodiments, the rotation mechanism can comprise a handle directly connected to the actuation shaft. For example, a proximal end of the actuation shaft can be connected to a handle 70" (FIG. 1) extending proximally from the housing. Rotation of the handle relative to the longitudinal axis rotates the actuation shaft to configure the handle assembly in one of an open/close mode, a forward mode, or a reverse mode.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of claims which follow.

What is claimed is:

1. A handle assembly for a surgical stapler comprising an elongate shaft having a proximal end and a distal end, the elongate shaft defining a longitudinal axis between the proximal end and the distal end, and a jaw assembly disposed at the distal end of the elongate shaft, the handle assembly comprising:
   a housing;
   a stationary handle disposed on the housing;
   a movable handle pivotably coupled to the housing and pivotable between an open position spaced apart from the stationary handle and a closed position adjacent the stationary handle;
   an actuation mechanism comprising:
      an advancing driver operably coupled to the movable handle and translatable distally with respect to the longitudinal axis responsive to movement of the movable handle from the open position to the closed position;
      a reversing driver operably coupled to the movable handle and translatable proximally with respect to the longitudinal axis responsive to movement of the movable handle from the open position to the closed position; and
      an actuation shaft extending along the longitudinal axis, the actuation shaft rotatably coupled to the housing with respect to the longitudinal axis, and the actuation shaft comprising:
         an advancing surface extending longitudinally along the actuation shaft; and
         a reversing surface extending longitudinally along the actuation shaft, the reversing surface angularly offset from the advancing surface; and
      wherein the actuation shaft is rotatable with respect to the longitudinal axis between a first orientation in which the advancing driver engages the advancing surface and a second orientation in which the reversing driver engages the reversing surface; and
   a coupler adapted to engage the elongate shaft of the surgical stapler.

2. The handle assembly of claim 1, wherein the actuation mechanism further comprises an idler operably coupled to the movable handle, the advancing driver, and the reversing driver.

3. The handle assembly of claim 1, further comprising a rotation mechanism to selectively rotate the actuation shaft between the first orientation and the second orientation.

4. The handle assembly of claim 1, wherein the coupler comprises a bayonet connector.

5. The handle assembly of claim 1, wherein the advancing driver comprises a pawl and the advancing surface comprises a first rack formed on the actuation shaft.

6. The handle assembly of claim 5, wherein the reversing driver comprises a pawl and the reversing surface comprises a second rack formed on the actuation shaft.

7. A handle assembly for a surgical stapler, the handle assembly comprising:
   a housing;
   a trigger pivotably coupled to the housing; and
   an actuation mechanism comprising:
      a forward driver operably coupled to the trigger;
      a reverse driver operably coupled to the trigger;
      an actuation shaft having a longitudinal axis, the actuation shaft rotatably coupled to the housing relative to the longitudinal axis, the actuation shaft comprising a forward interface surface and a reverse interface surface angularly offset from the forward interface surface, wherein the actuation shaft is rotatable relative to the longitudinal axis between a first orientation in which the forward interface surface engages the forward driver to move the actuation shaft in a first direction responsive to pivotable movement of the trigger and a second orientation in which the reverse interface surface engages the reverse driver to move the actuation shaft in a second direction opposite the first direction responsive to pivotable movement of the trigger; and
      a selector operably coupled to the actuation shaft to selectively rotate the actuation shaft relative to the longitudinal axis between the first orientation and the second orientation.

8. The handle assembly of claim 7, wherein the selector comprises:
   a slider extending transversely through the housing relative to the longitudinal axis of the actuation shaft, the slider slidable between a first position in which the actuation shaft is in the first orientation and a second position in which the actuation shaft is in the second orientation.

9. The handle assembly of claim 8, wherein the selector further comprises:
   a rack movable by the slider; and
   a gear engaged with the rack and rotationally coupled to the actuation shaft.

10. The handle assembly of claim 7, wherein the selector comprises:
    a switch selectively longitudinally slidable with respect to the longitudinal axis of the actuation shaft;
    a hub collar operably coupled to the switch, rotationally fixed to the housing, and positioned around the actuation shaft, the hub collar having a first edge and a second edge and comprising:
       a plurality of ramps formed in the first edge; and
       a plurality of recesses formed in the second edge; and
    a first plurality of projections extending radially outward from the actuation shaft at a location adjacent the first edge of the hub collar; and a second plurality of projections extending radially outward from the actuation shaft at a location adjacent the second edge of the hub collar;

the first plurality of projections and second plurality of projections positioned such that sliding the switch in a first direction engages each of the first plurality of projections with a corresponding one of the ramps and rotates the actuation shaft with respect to the housing and returning the switch in a second direction opposite the first direction engages each of the second plurality of projections within a corresponding recess.

11. The handle assembly of claim 10, wherein the switch is biased in the second direction.

12. The handle assembly of claim 7, wherein the selector comprises a handle rotationally fixed to the actuation shaft.

13. The handle assembly of claim 12, wherein the actuation shaft has a proximal end and a distal end and wherein the handle extends from the distal end of the actuation shaft.

* * * * *